United States Patent
Lu et al.

(10) Patent No.: US 6,417,161 B1
(45) Date of Patent: Jul. 9, 2002

(54) AMINO ACID AMIDINOHYDRAZONES, ALKOXYGUANIDINES AND AMINOGUANIDINES AS PROTEASE INHIBITORS

(75) Inventors: Tianbao Lu; Bruce E. Tomczuk, both of Collegeville; Thomas P. Markotan, Morgantown, all of PA (US); Richard M. Soll, Lawrenceville, NJ (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 0 days.

(21) Appl. No.: 09/296,296

(22) Filed: Apr. 22, 1999

Related U.S. Application Data
(60) Provisional application No. 60/082,969, filed on Apr. 24, 1998.

(51) Int. Cl.[7] .................. A61K 38/05; C07D 405/00
(52) U.S. Cl. .............. 514/2; 514/19; 514/20; 514/349; 546/283.7; 546/297
(58) Field of Search ............... 514/21, 19, 20, 514/349; 546/283.7, 297

(56) References Cited

U.S. PATENT DOCUMENTS

| | | | |
|---|---|---|---|
| 4,346,078 A | 8/1982 | Bajusz et al. | 424/177 |
| 4,418,052 A | 11/1983 | Wong | 424/1.1 |
| 4,499,082 A | 2/1985 | Shenvi et al. | 514/2 |
| 4,727,064 A | 2/1988 | Pitha | 514/58 |
| 4,764,604 A | 8/1988 | Müller | 536/103 |
| 5,011,686 A | 4/1991 | Pang | 424/94.1 |
| 5,024,998 A | 6/1991 | Bodor | 514/58 |
| 5,122,361 A | 6/1992 | Kung et al. | 424/1.1 |
| 5,466,811 A | 11/1995 | Alexander | 546/283 |
| 5,602,253 A | 2/1997 | Antonsson et al. | 544/330 |
| 5,614,499 A | 3/1997 | Bylund et al. | 514/19 |
| 5,656,600 A | 8/1997 | Abelman et al. | 514/13 |
| 5,705,487 A | 1/1998 | Schacht et al. | 514/19 |
| 5,891,909 A | 4/1999 | Soll et al. | 514/517 |
| 6,037,356 A * | 3/2000 | Lu et al. | 514/349 |

FOREIGN PATENT DOCUMENTS

| | | |
|---|---|---|
| CA | 2 164 684 | 6/1996 |
| EP | 0 468 231 B1 | 1/1992 |
| EP | 0 530 167 A1 | 3/1993 |
| EP | 0 604 022 A1 | 6/1994 |
| EP | 0 761 251 A1 | 3/1997 |
| WO | WO 92/04371 | 3/1992 |
| WO | 93/11152 * | 6/1993 |
| WO | WO 95/07291 | 3/1995 |
| WO | WO 95/23609 | 9/1995 |
| WO | WO 95/35309 | 12/1995 |
| WO | WO 96/11668 | 4/1996 |
| WO | WO 96/25426 | 8/1996 |
| WO | WO 96/32143 | 10/1996 |
| WO | WO 96/38136 | 12/1996 |
| WO | WO 97/02284 | 1/1997 |
| WO | WO 97/23499 | 7/1997 |
| WO | WO 97/46577 | 12/1997 |
| WO | WO 98/23565 | 6/1998 |

OTHER PUBLICATIONS

Thrombosis Research vol. 85, No. 2 pp. 133–145, Jan. 1997.*

Barrett, A.J., "Proteinase inhibitors: potential drugs?" *Enzyme Inhibitors as Drugs*, Sandler, M., ed., The MacMillan Press Ltd., London, England, pp. 219–229 (1980).

Baugh, R.J. and J. Travis, "Human Leukocyte Granule Elastase: Rapid Isolation and Characterization," *Biochemistry* 15:836–841 (1976).

Bergeron, R.J. and J.S. McManis, "Total Synthesis of (±)-15-Deoxyspergualin," *J. Org. Chem.* 52:1700–1703 (1987).

Bernatowicz, M.S. et al., "H–Pyrazole–1–carboxamidine Hydrochloride: An Attractive Reagent for Guanylation of Amines and Its Application to Peptide Synthesis," *J. Org. Chem.* 57:2497–2502.

Bernatowicz, M.S. et al., "Urethane Protected Derivatives of 1–Guanylpyrazole for the Mild and Efficient Preparation of Guanidines," *Tetrahedron Letters.* 34:3389–3392 (1993).

Blombäck, et al., "Synthetic Peptides with Anticoagulant and Vasodilating Activity," *Scand. J. Clin. Lab. Invest. Suppl.* 107:59–64 (19692).

(List continued on next page.)

Primary Examiner—Bennett Celsa
(74) Attorney, Agent, or Firm—Sterne, Kessler, Goldstein & Fox, P.L.L.C.

(57) ABSTRACT

The present invention is directed to aminoguanidine and alkoxyguanidine compounds, including compounds of Formula I:

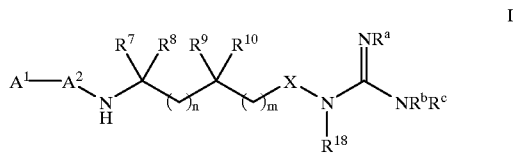

wherein X is O or $NR^{19}$ and $A^1, A^2, R^7-R^{10}, R^{18}, R^a, R^b, R^c$, n and m are set forth in the specification, as well as hydrates, solvates or pharmaceutically acceptable salts thereof, that inhibit proteolytic enzymes such as thrombin. Also described are methods for preparing the compounds of Formula I. Certain of the compounds exhibit antithrombotic activity via direct, selective inhibition of thrombin, or are intermediates useful for forming compounds having antithrombotic activity. The invention includes a composition for inhibiting loss of blood platelets, inhibiting formation of blood platelet aggregates, inhibiting formation of fibrin, inhibiting thrombus formation, and inhibiting embolus formation in a mammal. Other uses of compounds of the invention are as anticoagulants either embedded in or physically linked to materials used in the manufacture of devices used in blood collection, blood circulation, and blood storage.

39 Claims, No Drawings

OTHER PUBLICATIONS

Bodor, N. and J.H. Miller, "Novel Approaches in Prodrug Design," *Drugs in the Future VI*:165–182 (1981).

Bundgaard, H., "Design of prodrugs: Bioreversible derivatives for various functional groups and chemical entitles," in *Design of Prodrugs,* Bundgaard, H., ed., Elsevier Science Publisher B. V., Amsterdam, The Netherlands, pp. 1–92 (1985).

Cuypers, H.T. et al., "Sulfhydryl Content of Bovine Eye Lens Leucine Aminopeptidase," *J. Biol. Chem.* 257:7086–7091 (1982).

Jeong, J.-H. et al., "Cyclic Guanidino–Sugars with Low $pK_a$ as Transition–State Analog Inhibitors of Glycosidases: Neutral Instead of Charged Species Are the Acitve Forms," *J. Am. Chem. Soc. 118*:4227–4234 (1996).

Kim, K.S. et al., "Preparation of Argatroban Analog Thrombin Inhibitors with Reduced Basic Guanidine Moiety, And Studies of Their Cell Permeability and Antithrombotic Activities," *Med. Chem. Res. 6* :377–383 (1996).

Miller, A.E. and J.J. Bischoff, "A Facile Conversion of Amino Acids to Guanidino Acids," *Synthesis 9*:777–779 (1986).

Notari, R.E., "Theory and Practice of Prodrug Kinetics," *Methods Enzymol. 112*:309–323 (1985).

Powers, W.J. et al., "Indium–111 platelet scintigraphy in cerebrovascular disease," *Neurology 32*:938–943 (1982).

Saulnier, M.G. et al., "An Efficient Method for the Synthesis of Guanidino Prodrugs," *Bioorg. & Med. Chem. Lett.4*:1985–1990 (1994).

Thakur, M.L. et al., "Indium–111 Labeled Platelets: Studies on Preparation and Evaluation of In Vitro and In Vivo Functions," *Thromb. Res. 9*:345–357 (1976).

English language abstract of EP 0 468 231 B1 (Document AL1), Derwent World Patents Index, WPI Accession No. 92–034039/199205.

English language abstract of WO 96/25426 (Document AP2), Derwent World Patents Index, WPI Accession No. 96–393337/199639.

English language abstract WO 96/32143 (Document AL3). Derwent World Patents Index, WPI Accession No. 96–476853/199647.

* cited by examiner

AMINO ACID AMIDINOHYDRAZONES, ALKOXYGUANIDINES AND AMINOGUANIDINES AS PROTEASE INHIBITORS

This application claims the benefit, under 35 U.S.C. §119(e), of the earlier filing date of U.S. Provisional Application No. 60/082,969, filed on Apr. 24, 1998, the contents of which are fully incorporated by reference herein.

BACKGROUND OF THE INVENTION

1. Field of the Invention

This invention relates to new inhibitors of trypsin-like serine proteases, their synthesis, pharmaceutical compositions containing the compounds as active ingredients, and the use of the compounds as thrombin inhibitors and anticoagulants and as antiinflammatory inhibitors.

2. Related Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs*, Sandler, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

Inhibitors of thrombin based on the amino acid sequence around the cleavage site for the fibrinogen Aα chain were first reported by Blowback et al, *J. Clin. Lab. Invest.* 24, suppl.:107, 59 (1969), who suggested the sequence Phe-Val-Arg (P9-P2-P1, herein referred to as the P3-P2-P1 sequence) to be the best inhibitor.

U.S. Pat. No. 4,346,078 discloses the thrombin inhibitor H-DPhe-Pro-Agm, a dipeptidyl derivative with an aminoalkyl guanidine in the P1-position.

A number of dipeptidyl analogs of H-DPhe-Pro-Arg, and their use as thrombin inhibitors are described in U.S. Pat. Nos. 5,602,253, 5,614,499 and PCT Published Appl. No. WO 97/46577.

Inhibitors of thrombin based on peptide derivatives with a cyclic aminoalkyl guanidine, e.g. 3-aminomethyl-1-amidinopiperidine, in the P1-position have been disclosed in EP-A2-0,468,231.

Inhibitors of kininogenases that comprise a dipeptide linked to aminoalkyl guanidines are disclosed in PCT Published Appl. No. WO 95/07291.

PCT Published Appl. No. WO 92/04371 describing kininogenase inhibitors, e.g. kallikrein inhibitors based on derivatives of arginine.

EP-A1-0,530,167 describing a:-alkoxy ketone derivatives of arginine as thrombin inhibitors.

In vivo diagnostic imaging methods for intravascular thrombi have been previously reported. These imaging methods use compounds that are detectably labeled with radioactive or paramagnetic atoms. For example, platelets labeled with the gamma emitter, In-111, can be employed as an imaging agent for detecting thrombi (Thakur, M. L. et al., *Thromb Res.* 9:345 (1976); Powers et al., *Neurology* 32:938 (1982)). The thrombolytic enzyme streptokinase labeled with Tc-99m has been proposed as an imaging agent (Wong, U.S. Pat. No. 4,418,052 (1983)). The fibrin-binding domains of *Staphylococcus aureus* derived protein A labeled with the gamma emitters, I-125 and I-131, have been proposed as imaging agents (Pang, U.S. Pat. No. 5,011,686 (1991)). Radiolabeled and paramagnetically labeled alpha-ketoamide derivatives have also been proposed as thrombus imaging agents (Abelman et al., U.S. Pat. No. 5,656,600).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

SUMMARY OF THE INVENTION

The present invention is directed to novel compounds having Formula I (below). Also provided are processes for preparing compounds of Formula I. The novel compounds of the present invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin, or are intermediates useful for forming compounds having antithrombotic activity.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

Also provided are methods of inhibiting or treating aberrant proteolysis in a mammal, and methods for treating myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

In another aspect, the present invention includes compositions which are useful for in vivo imaging of thrombi in a mammal, comprising a compound of the present invention which is capable of being detected outside the body. Preferred are compositions comprising a pharmaceutically acceptable carrier and a diagnostically effective amount of a compound of the present invention and a detectable label, such as a radioactive atom.

In another aspect, the present invention includes methods which are useful for in vivo imaging or thrombi in a mammal.

DETAILED DESCRIPTION OF THE PREFERRED EMBODIMENTS

A first aspect of the present invention is directed to compounds of the general Formula I, including stereoisomers:

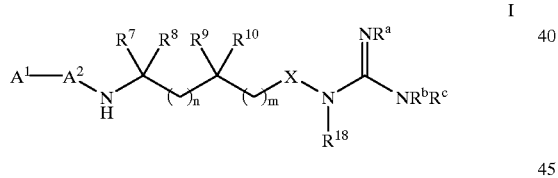

I or a solvate, hydrate or pharmaceutically acceptable salt thereof; wherein:

$A^1$ represents a structural fragment of Formula IIa, IIb, IIc, IId, IIe, IIf or IIg:

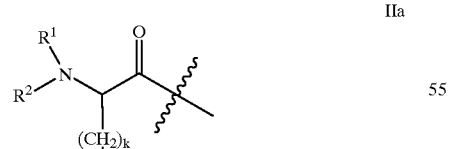

IIa

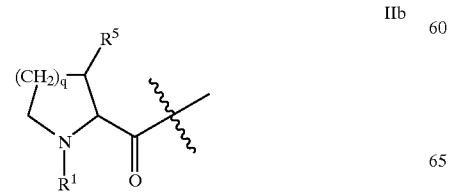

IIb

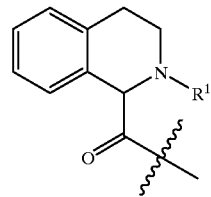

IIc

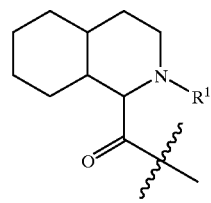

IId

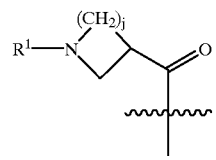

IIe

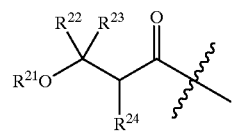

IIf

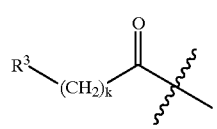

IIg wherein:
k is an integer 0, 1, 2, 3 or 4;
j is an integer 1, 2, 3 or 4;
q is an integer 0, 1 or 2 or 3;
$R^1$ represents H, $C_{1-4}$ alkyl or $R^{11}OOC$—$(C_{1-4})$alkyl-, optionally substituted in the position which is alpha to the carbonyl group, with a group $R^{14}$—$(CH_2)_p$—, wherein p is 0, 1 or 2 and $R^{14}$ is methyl, phenyl, OH, $COOR^{12}$, $CONHR^{12}$, where $R^{12}$ is H or $C_{1-4}$ alkyl group, and $R^{11}$ is H, $C_{1-6}$ alkyl, or benzyl substituted in the 4-position by $COOR^{12}$, where $R^{12}$ is as defined above, or $R^1$ represents $R^{13}$—NH—CO—$(C_{1-4})$alkyl-, optionally substituted alpha to the carbonyl with $C_{1-4}$ alkyl and where $R^{13}$ is H, $C_{1-4}$ alkyl or —$CH_2COOR^{12}$, where $R^{12}$ is as defined above, or $R^1$ represents $R^{12}OOC$—$CH_2$—OOC-alkyl-, where the alkyl group has 1 to 4 carbon atoms and is optionally substituted alpha to the carbonyl with $C_{1-4}$ alkyl and where $R^{12}$ is as defined above, or $R^1$ represents $C_{1-4}$ alkylsulfonyl, Ph(4-$COOR^{12}$)—$SO_2$—, Ph(3-$COOR^{12}$)—$SO_2$—, Ph(2-$COOR^{12}$)—$SO_2$—, where $R^{12}$ is as defined above, or $R^1$ represents $C_{1-4}$ alkylcarbonyl, or $R^1$ represents $C_{1-4}$ alkoxycarbonyl, or $R^1$ represents —CO—$(CH_2)_p$—$COOR^{12}$, where $R^{12}$ is as defined above and p is an integer 0, 1 or 2, or $R^1$ represents —$CH_2PO(OR^{15})_2$, —$CH_2SO_3H$ or —$CH_2$-(5-(1H)-tetrazolyl), where $R^{15}$ is, individually at each occurrence, H, methyl or ethyl;

$R^2$ represents H or $C_{1-4}$ alkyl, carboxy($C_{1-4}$)alkyl or $C_{1-4}$ alkoxycarbonyl($C_{1-4}$)alkyl;

$R^3$ represents $C_{1-4}$ alkyl, optionally having one or more fluorine atoms, or $R^3$ represents cyclopentyl, cyclohexyl or phenyl, any of which may be optionally substituted with $C_{1-4}$ alkyl, or $R^3$ represents fluoren-9-yl, or 9-hydroxyfluoren-9-yl, or $R^3$ represents a phenyl group substituted with one to three $OR^{16}$, where $R^{16}$ is independently H or $C_{1-4}$ alkyl and k is 0, 1, or $R^3$ represents a 1-naphthyl or 2-naphthyl group and k is 0, 1, or $R^3$ represents a cis- or trans-decalin group and k is 0, 1, or $R^3$ represents 4-pyridyl, 3-pyrrolidyl or 3-indolyl, any of which is optionally substituted with $OR^{16}$, where $R^{16}$ is as defined above and k is 0, 1, or $R^3$ represents $Si(Me)_3$ or $CH(R^{17})_2$, wherein $R^{17}$ is independently $C_{1-4}$ alkyl, cyclopentyl, cyclohexyl, benzyl or phenyl, or, in Formula IIa, where one $R^{17}$ is cyclopentyl, cyclohexyl or phenyl, and the other $R^{17}$ forms an ethylene bridge together with $R^1$ and k is 0, 1, or 2;

$R^5$ represents $C_{1-4}$ alkyl, phenyl, or benzyl;

$R^{21}$ represents H, $C(O)R^{41}$, $SiR^{42}R^{43}R^{44}$ or $C_{1-6}$ alkyl which latter group is optionally substituted or terminated by one or more substituents selected from $OR^{45}$ or $(CH_2)_tR^{46}$;

$R^{42}$, $R^{43}$ and $R^{44}$ independently represent H, phenyl or $C_{1-6}$ alkyl;

$R^{46}$ represents $C_{1-4}$ alkyl, phenyl, OH, $C(O)OR^{47}$ or $C(O)N(H)R^{48}$;

$R^{48}$ represents H, $C_{1-4}$ alkyl or $CH_2C(O)OR^{49}$;

$R^{45}$ and $R^{47}$ independently represent H, $C_{1-4}$ alkyl or $C_{7-9}$ alkylphenyl;

$R^{41}$ and $R^{49}$ independently represent H or $C_{1-4}$ alkyl; and t represents 0, 1 or 2;

$R^{22}$ and $R^{23}$ independently represent H, $C_{1-4}$ alkyl, cyclohexyl or phenyl;

$R^{24}$ represents a structural fragment of Formula IVa, IVb or IVc,

IVa

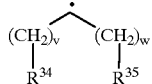

IVb

IVc

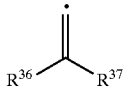

wherein v, w and u independently represent 0, 1, 2, 3 or 4;

$R^{34}$ and $R^{35}$ independently represent H, $Si(Me)_3$, 1- or 2-naphthyl, a polycyclic hydrocarbyl group, $CHR^{31}R^{32}$ or $C_{1-4}$ alkyl (which latter group is optionally substituted by one or more fluorine atoms), or $C_{3-8}$ cycloalkyl, phenyl, methylenedioxyphenyl, benzodioxanyl, benzofranyl, dihydrobenzofuranyl, benzothiazolyl, benzoxazolyl, benzimidazolyl, coumaranonyl, coumarinyl or dihydrocoumarinyl (which latter twelve groups are optionally substituted by one or more of $C_{1-4}$ alkyl (which latter group is optionally substituted by one or more halo substituent), $C_{1-4}$ alkoxy, halo, hydroxy, cyano, nitro, $SO_2NH_2$, $C(O)OH$ or $N(H)R^{33}$); $R^{31}$ and $R^{32}$ independently represent cyclohexyl or phenyl; $R^{36}$ and $R^{37}$ independently represent H, $C_{1-4}$ alkyl, $C_{3-8}$ cycloalkyl, phenyl (which latter group is optionally substituted by one or more of $C_{1-4}$ alkyl (which latter group is optionally substituted by one or more halo substituent), $C_{1-4}$ alkoxy, halo, hydroxy, cyano, nitro, $SO_2NH_2$, $C(O)OH$ or $N(H)R^{38}$) or together with the carbon atom to which they are attached form a $C_{3-8}$ cycloalkyl ring; $R^{33}$ and $R^{38}$ independently represent H or $C(O)R^{39}$; and $R^{39}$ represents H, $C_{1-4}$ alkyl or $C_{1-4}$ alkoxy;

$A^2$ represents a structural fragment of Formula IIIa, IIIb or IIIc:

IIIa

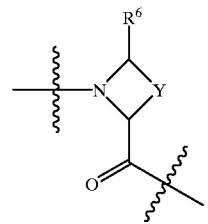

IIIb

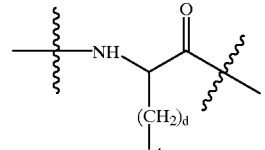

IIIc

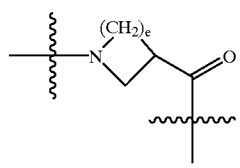

wherein d is 0, 1 or 2;

e is 1, 2, 3 or 4;

Y represents a methylene group, or

Y represents an ethylene group and the resulting 5-membered ring may optionally carry one or two fluorine atoms, a hydroxy group or an oxo group in position 4, or may or may not be unsaturated, or Y represents —$CH_2$—O—, —$CH_2$—S—, —$CH_2$—SO—, with the heteroatom functionality in position 4, or Y represents a n-propylene group and the resulting 6-membered ring may optionally carry in position 5 one fluorine atom, a hydroxy group or an oxo group, carry two fluorine atoms in one of positions 4 or 5 or be unsaturated in position 4 and 5, or carry in position 4 a $C_{1-4}$ alkyl group, or Y represents —$CH_2$—O—$CH_2$—, —$CH_2$—S—$CH_2$—, —$CH_2$—SO—$CH_2$—, or Y represents —$CH_2$—$CH_2$—$CH_2$—$CH_2$—;

$R^4$ is as defined as for $R^3$ above;

$R^6$ represents H or $C_{1-4}$ alkyl, carboxy, $C_{1-4}$ alkoxycarbonyl, carboxy($C_{1-4}$)alkyl or $C_{1-4}$ alkoxycarbonyl($C_{1-4}$)alkyl;

provided that when $A^1$ is a fragment of Formula IIb, and $A^2$ is a fragment of Formula IIIb, then $R^4$ is not 1-naphthyl or 2-naphthyl;

$R^7$ is one of hydrogen, alkyl, aralkyl, aryl, hydroxyalkyl, aminoalkyl, monoalkylaminoalkyl, diakylariinoalkyl, carboxyalkyl, hydroxy, alkoxy, aralkoxy, aryloxy, heteroaryloxy, or mono- or di-alkylamino, provided that n is other than zero when $R^7$ is hydroxy, alkoxy, aralkoxy, aryloxy, heteroaryloxy, or mono- or di-alkylamino;

$R^8$, $R^9$ and $R^{10}$ are each independently one of hydrogen, alkyl, aralkyl, aryl, hydroxyalkyl, aminoalkyl, monoalkylaminoalkyl, dialkylaminoalkyl or carboxyalkyl;

or $R^7$ and $R^8$ are taken together to form —$(CH_2)_i$—, where i is zero (a bond), 1 or 2, while $R^9$ and $R^{10}$ are defined as above; or $R^7$ and $R^{10}$ are taken together to form —$(CH_2)_j$—, where j is zero (a bond), or 1 to 8, while $R^8$ and $R^9$ are defined as above; or $R^9$ and $R^{10}$ are taken together to form —$(CH_2)_h$—, where h is 2–8, while $R^7$ and $R^8$ are defined as above;

$R^{18}$ is one of hydrogen, alkyl, alkenyl, alkynyl, aralkyl, aryl, hydroxyalkyl, aminoalkyl, monoalkylamino($C_{2-10}$)alkyl, dialkylamino($C_{2-10}$)alkyl or carboxyalkyl, or alternatively, $R^{18}$ and $R^{10}$ taken together to form —$(CH_2)_w$—, where w is 1–5;

X is oxygen, $NR^{19}$; or $CH=NR^{19}$, where the nitrogen of $CH=NR^{19}$ is attached to the nitrogen of $NR^{18}$;

$R^{19}$ is one of hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl;

$R^a$, $R^b$ and $R^c$ are independently hydrogen, alkyl, hydroxy, alkoxy, aryloxy, aralkoxy, alkoxycarbonyloxy, cyano or —$CO_2R^w$;

$R^w$ is alkyl, cycloalkyl, phenyl, benzyl,

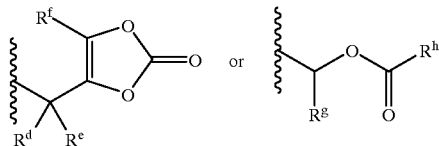

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n is from zero to 8; and m is from zero to 4.

Compounds of Formula I having S-configuration on the $A^2$ fragment are preferred ones. Compounds also having R-configuration on the $A^1$ fragment are particularly preferred ones.

The wavy lines on the carbon atom in the carbonyl group in Formulae IIa, IIb, IIc, IId, IIe, IIf, IIg, IIIa, IIIb, IIIc, and on the nitrogen atom in Formulae IIIa, IIIb, IIIc signify the bond position of the fragment.

The dots adjacent to the carbon atoms in fragments of Formula IVa, IVb and IVc signify the point of attachment of the fragments to the compound of Formula I.

Abbreviations are listed at the end of this specification.

Preferred values of $R^7$, $R^8$, $R^9$ and $R^{10}$ are independently one of hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl. Useful values of $R^7$, $R^8$, $R^9$ and $R^{10}$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl. Additional preferred compounds are those wherein $R^7$ and $R^8$ are taken together to form —$(CH_2)_i$— where i is preferably 2, 3 or 4. Another group of preferred compounds are those where $R^8$ and $R^9$ are taken together to form —$(CH_2)_h$— where h is most preferably 2.

$R^{18}$ preferably represents H or $C_{1-4}$ alkyl, carboxy, $C_{1-4}$ alkoxycarbonyl, carboxy($C_{1-4}$)alkyl, $C_{1-4}$ alkoxycarbonyl($C_{1-4}$)alkyl, ($C_{6-10}$)ar($C_{1-6}$)alkyl, or $C_{3-6}$alkenyl. Most preferred values of $R^{18}$ are hydrogen or $C_{1-6}$ alkyl or alternatively, $R^{18}$ and $R^{10}$ taken together to form —$(CH_2)_w$—, where w is 1–5.

A preferred value of X is O.

Also preferred is when X is $CH=NR^{19}$, where $R^{19}$ is preferably hydrogen, $C_{1-6}$ alkyl, optionally substituted with amino, mono($C_{1-4}$)alkylamino, $C_{1-6}$ alkoxy, hydroxy, carboxy, phenyl, $C_{1-4}$ alkyloxycarbonyl, $C_{6-10}$ ar($C_{1-4}$) alkoxycarbonyl, $C_{1-6}$acylamino, cyano, or trifluoromethyl.

Preferred values of $R^a$, $R^b$ and $R^c$ in Formula I are hydrogen, hydroxy, $C_{1-6}$alkyl, $C_{1-6}$ alkoxy, cyano or —$CO_2R^w$, where $R^w$, in each instance, is preferably one of $C_{1-4}$ alkyl, $C_{4-7}$ cycloalkyl or benzyloxycarbonyl. Suitable values of $R^a$, $R^b$ and $R^c$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$. In the most preferred embodiments, $R^a$, $R^b$ and $R^c$ are each hydrogen.

Also preferred at $R^a$, $R^b$ and $R^c$ is the group —$CO_2R^w$, where $R^w$ is one of

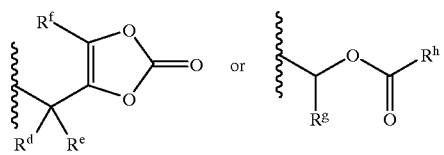

where $R^d$–$R^h$ are defined as above. When $R^a$, $R^b$ and $R^c$ are —$CO_2R^w$, where $R^w$ is one of one of these moieties, the resulting compounds are prodrugs that possess desirable formulation and bioavailability characteristics. A preferred value for each of $R^d$, $R^e$ and $R^g$ is hydrogen, $R^f$ is methyl, and preferred values for $R^h$ include benzyl and tert-butyl.

Preferred values of n in Formula I include from zero to 6, more preferably from zero to 4, and most preferably zero, 1 or 2. Preferred values of m include from zero to 4, more preferably zero, 1, 2 or 3.

According to the invention it has been found that compounds of the general Formula I, either as such or in the form of physiologically acceptable salts, and including stereoisomers, are potent serine protease inhibitors, wherein:

$A^1$ represents a structural fragment of Formula IIa, IIb, IIc, IId or IIg, preferably IIa, IIb or IIg; wherein:

k is an integer 0, 1, 2, 3 or 4, preferably 0, 1;

q is an integer 0, 1, 2 or 3, preferably 1;

$R^1$ represents H, $C_{1-4}$ alkyl, $R^{11}OOC$—($C_{1-4}$)alkyl-, optionally substituted in the position which is alpha to the carbonyl group, and the alpha substituent is a group $R^{14}$—$(CH_2)_p$—, wherein p is 0, 1 or 2 and $R^{14}$ is methyl, phenyl, OH, $COOR^{12}$, $CONHR^{12}$, where $R^{12}$ is H or $C_{1-4}$ alkyl, and $R^{11}$ is H or $C_{1-6}$ alkyl, or $R^1$ represents Ph(4-$COOR^{12}$)—$CH_2$—, where $R^{12}$ is as defined above, or $R^1$ represents $R^{13}$—NH—CO—($C_{1-4}$)alkyl-, and is optionally substituted alpha to the carbonyl with $C_{1-4}$ alkyl, and where $R^{13}$ is H or $C_{1-4}$ alkyl or —$CH_2COOR^{12}$ where $R^{12}$ is as defined above, or $R^1$ represents $R^{12}OOC$—$CH_2$—OOC—($C_{1-4}$)alkyl-, where the alkyl is optionally substituted alpha to the carbonyl with $C_{1-4}$ alkyl and where $R^{12}$ is as defined above, or $R^1$ represents $C_{1-4}$ alkylsulfonyl, Ph(4-$COOR^{12}$)—$SO_2$—, Ph(3-$COOR^{12}$)—SO—, Ph(2-$COOR^{12}$)—$SO_2$— where $R^{12}$ is as defined above or $R^1$ represents $C_{1-4}$ alkylcarbonyl, or $R^1$ represents $C_{1-4}$ alkoxycarbonyl, or $R^1$ represents —CO—$(CH_2)_p$—$COOR^{12}$, where $R^{12}$ is as defined above and p is an integer 0, 1 or 2, or $R^1$ represents —$CH_2PO(OR^{15})_2$, —$CH_2SO_3H$ or —$CH_2$—(5-(1H)-tetrazolyl), where $R^{15}$ is, individually at each occurrence, H, methyl or ethyl;

Preferably $R^1$ represents $R^{11}OOC$—($C_{1-4}$)alkyl-, and $R^{11}$ is H.

$R^2$ represents H or $C_{1-4}$ alkyl, carboxy($C_{1-4}$)alkyl or $C_{1-4}$alkoxycarbonyl($C_{1-4}$)alkyl;

$R^3$ represents $C_{1-4}$ alkyl, optionally substituted by one or more fluorine atoms, or $R^3$ represents cyclopentyl, cyclohexyl or phenyl, any of which may be optionally substituted with $C_{1-4}$ alkyl, or $R^3$ represents a 1-naphthyl or 2-naphthyl group and k is 0, 1, or $R^3$ represents a cis- or trans-decalin group and k is 0, 1, or $R^3$ represents Si(Me)$_3$ or CH($R^{17}$)$_2$, wherein $R^{17}$ is independently propyl, cyclopentyl, cyclohexyl, benzyl, or phenyl, or $R^3$ represents fluoren-9-yl or 9-hydroxy-fluoren-9-yl;

$A^2$ represents a structural fragment of Formula IIIa, IIIb or IIIc, preferably IIIa; wherein:
d is an interger 0, 1 or 2;
e is an integer 1, 2, 3 or 4, preferably 2, or 3;
Y represents a methylene group, or
Y represents an ethylene group and the resulting 5-membered ring may optionally carry one or two fluorine atoms, a hydroxy group or an oxo group in position 4, or may optionally be unsaturated, or
Y represents —$CH_2$—O—, —$CH_2$—S—, —$CH_2$—SO—, with the heteroatom functionality in position 4, or
Y represents a n-propylene group and the resulting 6-membered ring may optionally carry in position 5 one fluorine atom, a hydroxy group or an oxo group, carry two fluorine atoms in one of positions 4 or 5 or be unsaturated in position 4 and 5, or carry in position 4 a $C_{1-4}$ alkyl group, or
Y represents —$CH_2$—O—$CH_2$—, —$CH_2$—S—$CH_2$—, —$CH_2$—$SOCH_2$—, or
Y represents —$CH_2$—$CH_2CH_2$—$CH_2$—;
$R^4$ represents $C_{1-4}$ alkyl, or
$R^4$ represents a Si(Me)$_3$ group;
$R^6$ represents H or C, alkyl, preferably H or a methyl group, or $R^6$ represents —$(CH_2)_p$—$COOR^{51}$, where p is 0, 1 or 2 and $R^{51}$ is H or $C_{1-4}$alkyl, preferably p is 0 and $R^{51}$ is H;

$R^a$, $R^b$ and $R^c$ are each one of hydrogen, $C_{1-4}$ alkyl, hydroxy, $C_{1-4}$ alkoxy, phenoxy, $C_{1-4}$ alkyloxycarbonyl, benzyloxycarbonyl, cyano,

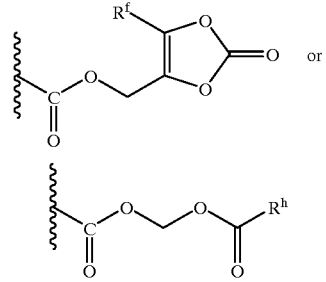

where $R^h$ is benzyl, methyl, ethyl, isopropyl, sec-butyl or t-butyl, and where $R^f$ is hydrogen or $C_{1-6}$ alkyl;

$R^7$, $R^8$, $R^9$ and $R^{10}$ are independently one of hydrogen, $C_{1-6}$ alkyl, $C_{2-10}$carboxyalkyl or $C_{2-10}$ hydroxyalkyl, or $R^7$ and $R^8$ are taken together to form —$(CH_2)_i$— where i is zero, 1 or 2, while $R^9$ and $R^{10}$ are defined as above; or $R^7$ and $R^{10}$ are taken together to form —$(CH_2)_j$—, where j is zero (a bond), or 1, 2 or 3, while $R^8$ and $R^9$ are defined as above; or $R^9$ and $R^{10}$ are taken together to form —$(CH_2)_h$—, where h is 2, 3, or 4, while $R^7$ and $R^8$ are defined as above;

$R^{18}$ is one of hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, mono($C_{1-4}$)alkylamino($C_{2-8}$)alkyl, di($C_{1-4}$)alkylamino($C_{2-8}$)alkyl or $C_{2-10}$ carboxyalkyl, or alternatively, $R^{18}$ and $R^{10}$ taken together to form —$(CH_2)_w$—, where w is 1–5;

X is —O—, —$NR^{19}$ or —CH=$NR^{19}$—;
$R^{19}$ is hydrogen or $C_{1-4}$ alkyl;
n is from zero to 4; and m is from zero to 4.

According to a preferred embodiment the invention relates to compounds of Formula I, wherein:

$A^1$ represents a structural fragment of Formula IIa, wherein:
k is 0 or 1;
$R^1$ represents $R^{11}OOC$—($C_{1-4}$)alkyl-, particularly methylene, ethylene and $R^{11}$ is H;
$R^2$ represents H;
$R^3$ represents a cyclohexyl group;
$A^2$ represents a structural fragment of Formula IIIa, wherein:
Y represents a methylene group, an ethylene group, or a n-propylene group and the resulting 6-membered ring may optionally carry in position 4 a $C_{1-4}$alkyl group, preferably Y represents methylene, ethylene; and
$R^6$ represents H;
$R^a$, $R^b$ and $R^c$ are hydrogen, hydroxy,

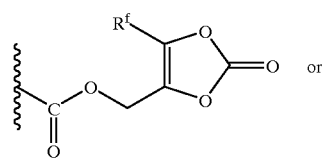

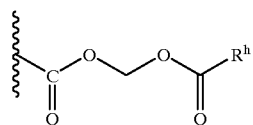

where $R^h$ is benzyl or t-butyl, and where $R^f$ is hydrogen or methyl;

$R^7$, $R^8$, $R^9$ and $R^{10}$ are independently one of hydrogen, $C_{1-6}$ alkyl, $C_{2-10}$hydroxyalkyl or $C_{2-10}$ carboxyalkyl, or $R^7$ and $R^8$ are taken together to form $(CH_2)_i$— where i is zero, 1 or 2, while $R^9$ and $R^{10}$ are defined as above; or $R^7$ and $R^{10}$ are taken together to form $-(CH_2)_j-$, where j is zero (a bond), or 1, 2 or 3, while $R^8$ and $R^9$ are defined as above; or $R^9$ and $R^{10}$ are taken together to form $-(CH_2)_h-$, where h is 2, 3 or 4, while $R^7$ and $R^8$ are defined as above;

$R^{18}$ is hydrogen, $C_{1-4}$ alkyl, $C_{2-4}$ hydroxyalkyl, $C_{2-4}$ carboxyalkyl, $C_{2-4}$aminoalkyl, dimethylamino($C_{2-8}$) alkyl, or methylamino($C_{2-8}$)alkyl;

X is —O—, —$NR^{19}$— or —CH=$NR^{19}$—, preferably O;

$R^{19}$ is hydrogen, or $C_{1-6}$ alkyl;

n is from zero to 4; and m is zero, 1, 2 or 3.

Additional preferred compounds of Formula I include those wherein:

$A^1$ represents a structural fragment of Formula IIf;

$R^{21}$ represents optionally substituted $C_{1-6}$ alkyl or, particularly, H;

$R^{24}$ represents a structural fragment of Formula IVa;

$A^2$ represents a structural fragment of Formula IIa;

Y represents $CH_2$ or $(CH_2)_2$—; and n represents 1.

Additional preferred compounds of Formula I include those wherein:

$A^1$ represents a structural fragment of Formula IIg;

k is zero or 1;

$R^3$ represents phenyl or benzyl, optionally substituted by one to three of $OR^{16}$, where $R^{16}$ is hydrogen or methyl, or $R^3$ represents fluoren-9-yl or 9-hydroxyfluoren-9-yl, or $R^3$ represents $CH(R^{17})_2$, where $R^{17}$ is cyclohexyl or phenyl;

$A^2$ represents a structural fragment of Formula IIIa;

Y represents $CH_2$ or $(CH_2)_2$;

n represents 1.

Compounds of Formula I having $A^2$ as a fragment

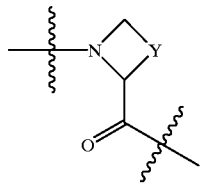

in the S-configuration are preferred. The wavy lines on the nitrogen and carbon atom in the above fragment signify the bond position of the fragment.

Most preferred compounds of the present invention have one of the Formulae Ia, Ib or Ic:

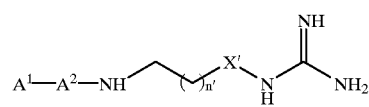

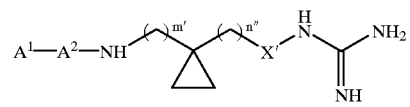

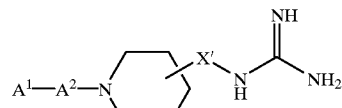

or a pharmaceutically acceptable salt thereof; where:

n' is 1, 2 or 3, preferably 1 or 2;

n" is 0, 1, 2 or 3, preferably 0 or 1;

m' is 0, 1, 2 or 3, preferably 0 or 1;

X' is —O—, —NH— or —CH=NH— (an amidinohydrazone group).

In this aspect of the present invention, combinations of $A^1$ and $A^2$ result in the following preferred $A^1$—$A^2$— fragments:

HOOC—$CH_2$—(R)Cgl-Aze—
HOOC—$CH_2$—$CH_2$—(R)Cgl-Aze—
HOOC—$CH_2$—(R)Cgl-Pro—
HOOC—$CH_2$—$CH_2$—(R)Cgl-Pro—
(HOOC—$CH_2$)$_2$—(R)Cgl-Pro—
H—(R)Cgl-Pic—
HOOC—$CH_2$—(R,S)CH(COOH)—(R)Cgl-Pic—
H—(R)Cha-Aze—
HOOC—$CH_2$—(R)Cha-Aze—
HOOC—$CH_2$—(RorS)CH(COOH)—(R)Cha-Aze—
HOOC—$CH_2CH_2$—(R)Cha-Aze—
HOOC—$CH_2$—NH—CO—$CH_2$—(R)Cha-Aze—
H—(R)Cha-Pro-Pab—
HOOC—$CH_2$—(R)Cha-Pro—
HOOC—$CH_2$-(Me)(R)Cha-Pro—
HOOC—$CH_2$—$CH_2$—(R)Cha-Pro—
HOOC—$CH_2$—$CH_2$-(Me)(R)Cha-Pro—
HOOC—$CH_2$—(RorS)CH(COOH)—(R)Cha-Pro—
HOOC—$CH_2$—NH—CO—$CH_2$—(R)Cha-Pro—
EtOOC—$CH_2$—$CH_2$—$CH_2$—(R)Cha-Pro—
Ph(4-COOH)—$SO_2$—(R)Cha-Pro—
H—(R)Cha-Pic—
HOOC—$CH_2$—(R)Cha-Pic—
HOOC—$CH_2$—(RorS)CH(COOH)—(R)Cha-Pic—
HOOC—$CH_2$—$CH_2$—(R)Cha-Pic—
HOOC—CO—(R)Cha-Pic—
HOOC—CH—CO—(R)Cha-Pic—
Me-OOC—$CH_2$—CO—(R)Cha-Pic—
$H_2$N—CO—$CH_2$—(R)Cha-Pic—
Boc-(R)Cha-Pic—
Ac-(R)Cha-Pic—
Me-$SO_2$—(R)Cha-Pic—
H—(R)Cha(R,S)betaPic—

HOOC—CH₂—CH₂—(R)Cha-(R,S)betaPic—
HOOC—CH₂—(R)Cha-Val—
HOOC—CH₂—CH₂—(R)Cha-Val—
H—(R)Hoc-Aze—
HOOC—CH₂—CH₂—(R)Hoc-Aze—
HOOC—CH₂—(R,S)CH(COOH)—(R)Hoc-Pro—
HOOC—CH₂—(R)Hoc-Pic—
(HOOC—CH₂)₂—(R)Hoc-Pic—
HOOC—CH₂—(R)Pro(3-(S)Ph)-Pro—
HOOC—CH₂—CH₂—(R)Pro(3-S)Ph)-Pro—
HOOC—CH₂—CH₂—(R)Tic-Pro—
HOOC—CH₂—CH₂—(R)Cgl-Aze—
HOOC—CH₂—(R)Cgl-Pro—
H—(R)Cha-Aze—
HOOC—CH₂—(R)Cgl-Aze—
H—(R)Cha-Pro—
H—(R)Cgl-Ile—
H—(R)Cgl-Aze—
HOOC—(R,S)CH(Me)-(R)Cha-Pro—
MeOOC—CH₂—(R)Cgl-Aze—
EtOOC—CH₂—(R)Cgl-Aze—
ⁿBuOOC—CH₂—(R)Cgl-Aze—
ⁿHexOOC—CH₂—(R)Cgl-Aze—
H—(R)Cgl-Pro—
HOOC—CH₂—(R)Cha-Pro—
HOOC—CH₂—CH₂—(R)Cgl-Pro—
HOOC—CH₂—CH₂—(R)Cha-Aze—
HOOC—CH₂—(R)Cha-Aze—
HOOC—CH₂—(R)Cha-Pro—
HOOC—CH₂—CH₂—(R)Cha-Pro—
(HOOC—CH₂)₂—(R)Cgl-Pro—
HOOC—CH₂—CH₂(HOOC—CH₂)—(R)Cha-Pro—
H—(R)Phe-Cha—
HOOC—CH₂—(R)Phe-Cha—
H—(R)Cha-Cha—
HOOC—CH₂—(R)Cha-Cha—
H—(R)Cha-Pro—
Me-(R)Cha-Pro—
HO—(CH₂)₃—(R)Cha-Pro—
HOOC—CH₂—(R)Cha-Pro—
ⁱPrOOC—CH₂—(R)Cha-Pro—
HOOC—CH₂-(Me)(R)Cha-Pro—
HOOC—(R,S)CH(Me)-(R)Cha-Pro—
HOOC—(R,S)CH(CH₂CH₂Ph)—(R)Cha-Pro—
HOOC—CH₂—CH₂—(R)Cha-Pro—
EtOOC—CO—(R)Cha-Pro—
(R,S)Bla-(R)Cha-Pro—
HOOC—CH₂—(nBu)(R)Cha-Pro—
HOOC—(R,S)CH(Me)-(R)Cha-Pro—
EtOOC—(R,S)CH(Me)HR)Cha-Pro—
HOOC—(R)CH(CH₂—OH)—(R)Cha-Pro—
HOOC—(R,S)CH(Ph)—(R)Cha-Pro—
HOOC—(S)CH(CH₂CH₂Ph)—(R)Cha-Pro—
HOOC—(R)CH(CH₂CH₂Ph)—(R)Cha-Pro—
HOOC—CO—(R)Cha-Pro—
MeOOC—CO—(R)Cha-Pro—
HOOC—(R,S)CH(CH₂COOH)—(R)Cha-Pro—
MeOOC—(R,S)CH(CH₂COOMe)—(R)Cha-Pro—
HOOC—Ph-4-CH₂—R)Cha-Pro—
(HO)₂P(O)—CH₂—(R)Cha-Pro—
EtO(HO)P(O)H₂—(R)Cha-Pro—
(EtO)₂P(O)—CH₂—(R)Cha-Pro—
H—(R,S)Pro(3-(trans)Ch)-Pro—
HOOC—CH₂—(R,S)Pro(3-(trans)Ph)-Pro—
N-fluoren-9-ylcarboxy-Pro—
N-(9-hydroxyfluoren-9-ylcarboxy)-Pro—
Dca-Pro—
Boc-Dca-Pro—
Dpa-Pro—
Boc-Dpa-Pro—
(Ph)₂CHCH₂C(O)-Pro—
(Ph)₂CHC(O)-Pro—
(Chx)₂CHCH₂C(O)-Pro—
(Chx)₂CHC(O)Pro—

Of those fragments, the following fragments are most preferred:
HOOCCH₂-(Me)(R)Cha-Pro—
HOOC—CH₂—(R)Cha-Pic—

Alternative embodiments of the present invention include compounds of Formula I in which two "R" groups together form a saturated or unsaturated hydrocarbon bridge, thus forming an additional cyclic moiety in the resulting compounds. Alternative embodiments include compounds of Formula I wherein $A^1$, $A^2$, m and n are as defined above; and, A. $R^{18}$ and $R^b$ are taken together to form —(CH₂)—(CH₂)ᵣ or =CH—N=CH—NH—, where r is 1, 2 or 3; $R^a$ is hydrogen or hydroxy;
$R^c$ is hydrogen, alkyl, hydroxy, alkoxy, aryloxy, aralkoxy, alkoxycarbamoyloxy, cyano or —CO₂Rʷ—, where Rʷ is as defined above;
$R^7$, $R^8$, $R^9$ and $R^{10}$ are independently one of hydrogen, $C_{1-6}$ alkyl, $C_{2-10}$ carboxyalkyl or $C_{2-10}$ hydroxyalkyl, or $R^7$ and $R^8$ are taken together to form —(CH₂)ᵢ— where i is zero, 1 or 2, while $R^9$ and $R^{10}$ are defined as above; or $R^7$ and $R^{10}$ are taken together to form —(CH₂)ⱼ—, where j is zero (a bond), or 1, 2 or 3, while $R^8$ and $R^9$ are defined as above; or $R^9$ and $R^{10}$ are taken together to form —(CH₂)ₕ—, where h is 2, 3, or 4, while $R^7$ and $R^8$ are defined as above; or B. $R^a$ and $R^c$ are taken together to form —CH₂—(CH₂)ₛ—, where s is 1 or 2;
$R^{18}$ is hydrogen, alkyl, alkoxy, aryloxy, aralkoxy, alkoxycarbonyloxy, cyano or —CO₂Rʷ—, where Rʷ is as defined above; and
$R^7$, $R^8$, $R^9$ and $R^{10}$ are independently one of hydrogen, $C_{1-6}$ alkyl, $C_{2-10}$ carboxyalkyl or $C_{2-10}$ hydroxyalkyl, or $R^7$ and $R^8$ are taken together to form —(CH₂)ᵢ— where i is zero, 1 or 2, while $R^9$ and $R^{10}$ are defined as above; or $R^7$ and $R^{10}$ are taken together to form —(CH₂)ⱼ— where j is zero (a bond), or 1, 2 or 3, while $R^8$ and $R^9$ are defined as above; or $R^9$ and $R^{10}$ are taken together to form —(CH₂)ₕ—, where h is 2, 3, or 4, while $R^7$ and $R^8$ are defined as above.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The compounds of Formula I may also be solvated, especially hydrated. Hydration may occur during manufacturing of the compounds or compositions comprising the compounds, or the hydration may occur over time due to the hygroscopic nature of the compounds.

Certain compounds within the scope of Formula I are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology*, 112:309–323 (1985); Bodor, N., "Novel Approaches in Prodrug Design," *Drugs of the Future*, 6(3):165–182 (1981); and Bundgaard, H., "Design of Prodrugs: Bioreversible-Derivatives for Various Functional Groups and Chemical Entities," in *Design of Prodrugs* (H. Bundgaard, ed.), Elsevier, New York (1985). Useful prodrugs are those where $R^a$, $R^b$ and/or $R^c$ are —$CO_2R^w$, where $R^w$ is defined above. See, U.S. Pat. No. 5,466,811 and Saulnier et al., *Bioorg. Med. Chem. Lett.* 4:1985–1990 (1994).

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive atom.

In another aspect, the present invention provides diagnostic compositions which are used for in vivo imaging of thrombi in a mammal, comprising a pharmaceutically acceptable carrier and a diagnostically effective amount of a compound or composition of the present invention.

In another aspect, the present invention includes methods which are useful for in vivo imaging or thrombi in a mammal.

According to a preferred aspect, useful compounds are those wherein the $R^1$ or $R^3$ substituent is substituted with a detectable label, such as a radioactive iodine atom, such as I-125, I-131 or I-123. In this aspect, $R^1$ is preferably phenyl, having a para I-123, para I-125 or para I-131 substitution, or benzyl, having a meta I-123, meta I-125 or meta I-131 substitution.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "heteroaryl" as employed herein refers to groups having 5 to 14 ring atoms; 6, 10 or $14\pi$ electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathienyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$ alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The terms "alkoxy" refers to any of the above alkyl groups linked to an oxygen atom.

The term "halogen" or "halo" as employed herein by itself or as part of another group refers to chlorine, bromine, fluorine or iodine with chlorine being preferred.

The term "monoalkylarnine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heterocyclic" is used herein to mean a saturated or wholly or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Especially useful are rings containing one oxygen or sulfur, one to three nitrogen atoms, or one oxygen or sulfur combined with one or two nitrogen atoms. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyirolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydroturyl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^yR^z$ moiety, wherein $R^y$ and $R^z$ are, independently from one another, hydrogen or $C_1$ to $C_8$ alkyl, or together with the nitrogen to which they are bound, form a saturated or unsaturated 5-, 6-, or 7-membered ring.

The term "heteroaryl" includes 5 or 6 membered aromatic heterocyclic rings containing one or more heteroatoms selected from nitrogen, sulphur and oxygen atoms, and fused bicyclic ring systems containing one or more nitrogen, sulfur, and oxygen atoms. Examples of such groups include oxadiazole, thiazole thiadiazole, triazole, tetrazole, benzimidazole, pyridine, furan and thiophene.

A $C_{3-7}$ cycloalkenyl group includes rings containing at least one double bond incorporated in the ring.

A $C_{3-7}$ heterocycloalkyl group includes rings containing one or more heteroatoms selected from nitrogen, sulphur and oxygen atoms, for example, a tetrahydropyran-4-yl group.

A $C_{3-7}$ heterocycloalkenyl group includes rings containing one or more heteroatoms selected from nitrogen, sulphur and oxygen atoms, together with at least on double bond incorporated in the ring.

Methods of Making

Preparation of Starting Materials/Protection Procedures/Deprotection Procedures

The following starting materials can be prepared by the methods described in U.S. Pat. No. 5,614,499, fully incorporated by reference herein:

Boc-(R)Pgl-OH
Boc-(R)Cha-OH
Boc-(R)Hop-OH
H-Pab(Z)×HCl
H-Pic-OEt×HCl
Boc-(R)Cgl-OH
Boc-(R)Hoc-OH
Boc-(R)Cgl-Aze-OH
Boc-(R)Cgl-Pic-OH
Boc-(R)Cgl-Pro-OH
Boc-(R)Cha-Aze-OH
Boc-(R)Cha-Pro-OH
Boc-(R)Cha-Pic-OH
Boc-(R)Cha-(R,S)betaPic-OH
Boc-(R)Cha-Val-OH
Boc-(R)Hoc-Aze-OH
Boc-(R)Hoc-Pro-OH
Boc-(R)Hoc-Pic-OH
Boc-(R)Pro-Phe-OH
Boc-(R)Pro(3-(S)Ph)-Pro-OH
Boc-(R)Tic-Pro-OH
Boc-(R)Cgl-Ile-OH
Boc-(R)Phe-Phe-OH
H-(R)Dph-OH
Boc-(R)Cgl-OH
Boc(R)Dch-OH
Boc-(Me)(R)Cha-OH
Boc-(R)Cha-Pro-OH
Boc-(R)Cha-Pic-OH
Boc-(R,S)Pro(3-(trans)Ph-Pro-OH
Boc-(R,S)Pro(3-(trans)Ch)-Pro-OH
Boc-(R)Hoc-OH
Boc-(R)Hoc-Pro-OH
Boc-(R)Hoc-Pic-OH
Boc-(R)Cha-Aze-OH
Boc-(R)Cha-Pic(4-(S)Me)-OH
Boc-(R)Cha-(R)Pic(4-(R)Me)-OH
Boc-(R)Cha-(R,S)Pic(4,5-dehydro)-OH
Boc-(R)Cgl-Pic-OH
Boc-(R)Dph-Pic-OH
Boc-(R)Dch-Pic-OH
Boc-(R)Cha-Pro(5-(S)Me)-OH Procedures for protection and deprotection of functional groups in starting materials and intermediates are described in U.S. Pat. No. 5,614,499, fully incorporated by reference herein.

Synthesis

Another aspect of the present invention is a process for preparing an amidinohydrazone compound of Formula I, comprising reacting an ,aminoguanidine of the formula:

$$\underset{H_2N}{\overset{R^{18}}{\underset{|}{N}}}\underset{NR^a}{\overset{}{C}}NR^bR^c \qquad \text{VII}$$

wherein $R^{18}$, $R^a$, $R^b$ and $R^c$ are defined as above, with a derivatized dipeptide of the formula:

$$P^b-A^1-A^2-\underset{R^7\ R^8}{\overset{H}{N}}\underset{}{\overset{}{C}}(\ )_n\overset{O}{\underset{R^9}{C}} \qquad \text{VIII}$$

wherein $P^b$ is an amino-protecting group, and $A^1$, $A^2$, $R^7$, $R^8$, $R^9$, and n are defined as above to form an amidinohydrazone, of Formula IX:

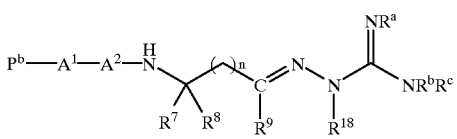

IX where $P^b$, $A^1$, $A^2$, $R^7$—$R^9$, $R^{18}$, $R^a$, $R^b$, $R^c$ and n are as defined above.

The aminoguanidine (Formula VII) is typically provided as a salt, preferably the nitrate salt. This step proceeds at ambient temperature using alcohol as a solvent. An acid, such as 4N HCl in dioxane is added to the reaction mixture. The reaction is more fully described herein.

The present invention is also directed to a process for preparing an aminoguanidine compound of Formula I, comprising selectively reducing the hydrazone carbon to nitrogen double bond of an amidinohydrazone of Formula IX. $P^b$ is an N-terminal amino protecting group, such as tert-butyloxy carbonyl or benzyloxy-carbonyl.

Another aspect of the present invention is a process for preparing a alkoxyguanidine compound of Formula I, comprising reacting an alkoxyamine derivatized dipeptide of the formula:

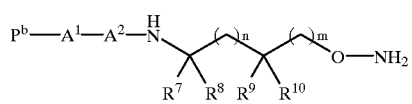

X wherein $P^b$, $A^1$, $A^2$, $R^7$—$R^{10}$, n and m are defined as above with a guanidinylating reagent. Preferred guanidinylating reagents include: aminoiminosulfonic acid, optionally substituted 1H-pyrazole-1-carboxamidines, or N,N'-bis(tert-butoxycarbonyl)S-methyl isothiourea.

In more detail, compounds of Formula I can be formed by the methods described in Schemes 4–6. Scheme 4 depicts a synthesis scheme for forming alkoxyguanidines (X is O) of Formula I, Scheme 5 depicts an alternate synthesis scheme for forming alkoxyguanidines of Formula I, and Scheme 6 depicts a synthesis scheme for forming aminoguanidines (X is $NR^{19}$) or amidinohydrazones (X is CH=$NR^{19}$) of Formula I With respect to these schemes, an N-terminally protected peptide, $P^a$—$A^2$ is coupled with an aminoalcohol using standard peptide coupling. The resulting intermediate is thereafter coupled to $P^b$—$A^1$ using standard peptide coupling techniques. Alternatively, $A^1$ and $A^2$ can be coupled, prior to coupling of $A^2$ and the aminoalcohol.

The alcohol is converted employing a Mitsunobu reaction with an N-hydroxycyclic imide derivative such as N-hydroxyphthalimide. Unveiling of the phthalimide protecting group is accomplished using standard conditions well known in the art (Greene, T. W. and Wuts, P. G. M., supra), for example, sodium borohydride in a mixture of an appropriate alcohol (e.g. ethanol or 2-propanol)/water followed by acidification. Alternatively, removal of the protecting group may be accomplished using hydrazine or methylamine.

Guanidinylation of the resulting alkoxy amine is achieved using standard reagents such as aminoiminosulfonic acid (Miller, A. E. and Bischoff, J. J. *Synthesis* 777 (1986)), or 1H-pyrazole-1-carboxamidines hydrochloride (Bernatowicz, M. S. et. al. *J. Org. Chem.* 57(8):2497 (1992)), or with substituted guanidinylating reagents such as N,N'-bis(tert-butoxycarbonyl)-S-methylisothiourea (Bergeron, R. J. and McManis, J. S. *J. Org. Chem.* 52:1700 (1987)) or N—$R^a$, N—$R^b$, N'$R^c$-1H-pyrazole-1-carboxamidine, where $R^a$, $R^b$ and $R^c$ are defined as above for Formula I. Useful 1H-pyrazole-1-carboxamidines include N,N'-bis(tert-butoxycarbonyl)-1H-pyrazole-1-carboxamidine and N,N'-bis(benzyloxycarbonyl)-1H-pyrazole-1-carboxamidine (all of which can be prepared according to Bernatowicz, M. S. et. al., *Tetrahedron Letters* 34:3389 (1993)).

Alternatively, peptide $P^a$—$A^2$ may be coupled directly to an aminoaldehyde or aminodiol using standard peptide coupling techniques. Or, dipeptide $P^b$—$A^1$—$A^2$ can be coupled to the aminoaldehyde or aminodiol.

The compound having a free aldehyde is then converted to amidinohydrazone using standard conditions, for example, treatment with an aminoguanidine, such as aminoguanidine or 2-hydrazinoimidazoline, optionally in the presence of an acid such as nitric acid, hydrogen chloride, or hydrogen bromide, in an appropriate solvent, for example, ethanol or methanol, which, in addition, may contain other solvents such as dichloromethane or tetrahydrofuran. Conversion of amidinohydrazone to aminoguanidine is accomplished under reducing conditions well known in the art, for example, lithium borohydride in an appropriate solvent such as tetrahydrofuran or methanol at various temperatures up to reflux. As an alternative method, catalytic hydrogenation with palladium on carbon catalyst can be employed.

When $R^a$, $R^b$ and/or $R^c$ are a protecting group, for example t-butyloxycarbonyl (Boc), these protecting groups can be optionally removed by treatment with acid, usually trifluoroacetic acid in a suitable solvent such as dichloromethane or water, or by HCl gas dissolved in a suitable solvent, such as 1,4-dioxane.

Compounds wherein $R^a$ and $R^c$ together form a cyclic group, such as an imidazoline, can be synthesized by employing an imidazoline in place of the aminoguanidine in the above schemes.

Compounds wherein $R^7$ and $R^{10}$ or $R^8$ and $R^{10}$ together form a methylene linkage can be synthesized by substituting a cyclic ketone having a reactive group L that is attached directly or indirectly to the carbocyclic ring. Examples of suitable reagents include 2-hydroxycyclopentanone, 3-hydroxycyclopentanone, 2-hydroxycyclohexanone and 3-hydroxycyclohexanone.

Compounds IX wherein $R^{18}$ and $R^b$, or $R^a$ and $R^c$ are taken together with the nitrogens to which they are attached to form a ring structure are prepared by substituting a heterocyclic amine XI or XII (below) for the aminoguanidine in the above schemes.

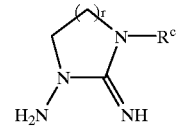

XI

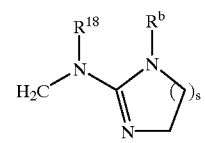

XII

According to the invention there is also provided a process for the preparation of compounds of Formula I which comprises:

(a) the coupling of a compound of Formula XV,

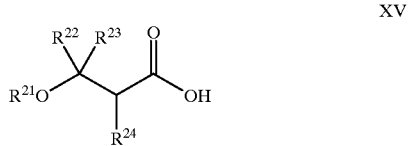

XV wherein $R^{21}$, $R^{22}$, $R^{23}$ and $R^{24}$ are as hereinbefore defined with a compound of Formula XVI,

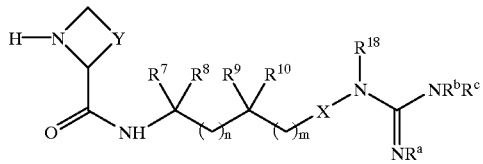

XVI wherein Y, $R^6$—$R^{10}$, n, m, X, $R^a$, $R^b$ and $R^c$ are as hereinbefore defined; or (b) the coupling of a compound of Formula XVII,

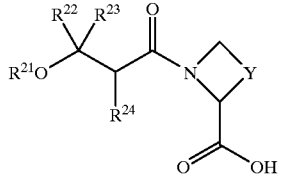

XVII wherein $R^{21}$, $R^{22}$, $R^{23}$, $R^{24}$ and Y are as hereinbefore defined with a compound of Formula XVIII,

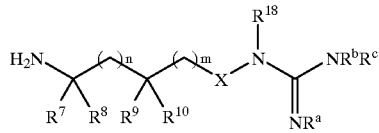

XVIII wherein $R^7$—$R^{10}$, $R^{18}$, n, m, X, $R^a$, $R^b$ and $R^c$ are as hereinbefore defined, for example in the presence of a coupling system (e.g. oxalyl chloride in DMF, EDC, DCC, HATU, or BOP), an appropriate base (e.g. pyridine, DMAP, TEA or DIEA) and a suitable organic solvent (e.g. dichloromethane, acetonitrile or DMF).

Compounds of Formula XV are commercially available, are well known in the literature, or are available using known techniques.

It will be appreciated by those skilled in the art that in the process described above the functional groups of intermediate compounds may need to be protected by protecting groups.

Functional groups which it is desirable to protect include hydroxy, amino and carboxylic acid. Suitable protecting groups for hydroxy include trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acid include $C_{1-6}$ alkyl or benzyl esters. Suitable protecting groups for amino, amidino and guanidino include t-butyloxycarbonyl or benzyloxy carbonyl. Amidino and guanidino nitrogens may be either mono- or diprotected.

The protection and deprotection of functional groups may take place before or after coupling.

In particular, the compounds of Formula I may be prepared by processes comprising the coupling of an N-acylated amino acid or a N-protected amino acid. When a N-protected amino acid is used the acyl group may be added after coupling and deprotection of the nitrogen atom may then be effected using standard methods thereafter.

Protecting groups may be removed in accordance with techniques which are well known to those skilled in the art and as described hereinafter.

The use of protecting groups is fully described in 'Protective Groups in Organic Chemistry', edited by J. W. F. McOmie, Plenum Press (1973), and 'Protective Groups in Organic Synthesis', $2^{nd}$ edition, T. W. Greene & P. G. M. Wuts, Wiley-Interscience (1991).

It will also be appreciated by those skilled in the art that, although such protected derivatives of compounds of Formula I may not possess pharmacological activity as such, they may be administered parenterally or orally and thereafter metabolized in the body to form compounds of the invention which are pharmacologically active. Such derivatives may therefore be described as "prodrugs." All prodrugs of compounds of Formula I are included within the scope of the invention.

Compounds of Formula I, pharmaceutically-acceptable salts, tautomers and stereoisomers thereof, as well as prodrugs thereof, are hereinafter referred to together as "the compounds of the invention."

Uses

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of Formula I with an organic or inorganic acid, preferably by contact in solution, or by any of the standard methods detailed in the literature available to any practitioner skilled in the art. Examples of useful organic acids are carboxylic acids such as maleic acid, acetic acid, trifluoroacetic acid, tartaric acid, propionic acid, fumaric acid, isethionic acid, succinic acid, cyclamic acid, pivalic acid and the like; useful inorganic acids are hydrohalide acids such as HCl, HBr, HI; sulfuric acid; phosphoric acid and the like. Preferred acids for forming acid addition salts include HCl, trifluoroacetic acid, and acetic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to inhibit trypsin-like proteases.

An end use application of the compounds that inhibit chymotrypsin and trypsin is in the treatment of pancreatitis. For their end-use application, the potency and other biochemical parameters of the enzyme-inhibiting characteristics of the compounds of the present invention is readily ascertained by standard biochemical techniques well known in the art. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit either factor Xa or thrombin may be employed for a number of therapeutic purposes. As factor Xa or thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA).

Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, blood lines and stents. The compounds of the present invention may also be used as an anticoagulant in extracorporeal blood circuits.

Metal stents have been shown to reduce restenosis, but are thrombogenic. A strategy for reducing the thrombogenicity of stents is to coat, embed, adsord or covalently attach a thrombin-inhibiting agent to the stent surface. The compounds of the present invention can be employed for this purpose. Compounds of the invention can be attached to, or embedded within soluble and/or biodegradeable polymers as and thereafter coated onto stent materials. Such polymers can include polyvinylpyrrolidone, polyhydroxypropylmethacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent 2,164,684 and PCT Published Applications WO 96/11668, WO 96/32143 and WO 96/38136.

By virtue of the effects of both factor Xa and thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement. The compounds of the present invention may be useful in treating neoplasia and metastasis as well as neurodegenerative diseases, such as Alzheimer's disease and Parkinson's disease.

When employed as thrombin or factor Xa inhibitors, the compounds of the present invention may be administered in an effective amount within the dosage range of about 0.1 to about 500 mg/kg, preferably between 0.1 to 10 mg/kg body weight, on a regimen in single or 2–4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

Human leucocyte elastase is released by polymorphonuclear leukocytes at sites of inflammation and thus is a contributing cause for a number of disease states. Compounds of the present invention are expected to have an anti-inflammatory effect useful in the treatment of gout, rheumatoid arthritis and other inflammatory diseases, and in the treatment of emphysema. The leucocyte elastase inhibitory properties of compounds of the present invention are determined by the method described below. Cathepsin G has also been implicated in the disease states of arthritis, gout and emphysema, and in addition, glomerulonephritis and lung infestations caused by infections in the lung. In their end-use application the enzyme inhibitory properties of the compounds of Formula I is readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15:836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4° C. A protein fraction precipitates during dialysis and is isolated by centrifugation. This fraction contains most of the chymotrypsin-like activity of leukocyte granules. Specific substrates are prepared for each enzyme, namely N-Suc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10 M Hepes buffer, pH 7.5, containing 0.50 M NaCl, 10% dimethylsulfoxide and 0.0020 M Suc-Ala-Ala-Pro-Phe-p-nitroanilide as a substrate. Hydrolysis of the p-nitroanilide substrate is monitored at 405 nm and at 25° C.

Useful dose range for the application of compounds of the present invention as neutrophil elastase inhibitors and as Cathepsin G inhibitors depend upon the nature and severity of the disease state, as determined by the attending diagnostician, with a range of 0.01 to 10 mg/kg body weight, per day, being useful for the aforementioned disease states.

Compounds of the present invention that inhibit urokinase or plasminogen activator are potentially useful in treating excessive cell growth disease state. As such compounds of the present invention may also be useful in the treatment of benign prostatic hypertrophy and prostatic carcinoma, the treatment of psoriasis, and as abortifacients. For their end-use application, the potency and other biochemical parameters of the enzyme inhibiting characteristics of compounds of the present invention are readily ascertained by standard biochemical techniques well known in the art. Actual dose ranges for this application will depend upon the nature and severity of the disease state of the patient or animal to be treated as determined by the attending diagnostician. It is to be expected that a general dose range will be about 0.0 1 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin inplasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of these assays by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred salts are hydrochloride and acetate salts. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Compounds of Formula I can be labeled with radioactive iodine as described below or by using an exchange reaction. Exchange of hot iodine for cold iodine is well known in the art. Alternatively, a radioiodine labeled compound can be prepared from the corresponding bromo compound via a tributylstannyl intermediate. See, U.S. Pat. No. 5,122,361, herein incorporated by reference.

The present invention also includes compositions which are useful for in vivo imaging of thrombi in a mammal, wherein the compositions are comprised of a compound of Formula I complexed with a radioactive atom.

The present invention also include diagnostic compositions which are useful for in vivo imaging of thrombi in a mammal, comprising a pharmaceutically acceptable carrier and a diagnostically effective amount of compositions derived from the compounds of Formula I.

The "diagnostically effective amount" of the composition required as a dose will depend on the route of administration, the type of mammal being treated, and the physical characteristics of the specific mammal under consideration. These factors and their relationship to determining this dose are well known to skilled practitioners in the medial diagnostic arts. Also, the diagnostically effective amount and method of administration can be tailored to achieve optimal efficacy but will depend on such factors as weight, diet, concurrent medication and other factors which those skilled in the medical arts will recognize. In any regard, the dose for imaging should be sufficient for detecting the presence of the imaging agent at the site of a thrombus in question. Typically, radiologic imaging will require that the dose provided by the pharmaceutical composition position of the present invention be about 5 to 20 $\mu$Ci, preferably about 10 $\mu$Ci. Magnetic resonance imaging will require that the dose provided be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

"Pharmaceutically acceptable carriers" for in vivo use are well known in the pharmaceutical art, and are described, for example, in *Remington's Pharmaceutical Sciences*, Mack Publishing Co. (A. R. Gennaro edit. 1985). The pharmaceutical compositions of the present invention may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

The present invention also encompasses diagnostic compositions prepared for storage or administration. These would additionally contain preservatives, stabilizers and dyes. For example, sodium benzoate, sorbic acid and esters of p-hydroxybenzoic acid may be added as preservatives. Id. At 1449. In addition, antioxidants and suspending agents may be used.

The in vivo imaging methods of the present invention also offer several advantages over previous imaging techniques for the detection or monitoring of the presence, size, regression or increase of a thrombus. In particular, the present invention provides compounds, compositions and diagnostic compositions have been designed to bind extremely tightly to the thrombin associated with a thrombus and thereby reduce "background" due to circulating radioactivity or paramagnetism arising from unbound imaging agent. Furthermore, in vivo imaging by intracoronary injection of the compounds, compositions or diagnostic compositions of the present invention, is expected to be almost instantaneous since these imaging agents would saturate the thrombin bound to the thrombus immediately.

Accordingly, the present invention also includes methods for in vivo imaging of a thrombus in a mammal, comprising the steps of: (1) administering to a mammal a diagnostically acceptable amount of a compound, composition, or diagnostic composition of the present invention and (2) detecting a thrombus in a blood vessel.

The term "in vivo imaging" as used herein relates to methods of the detection of a thrombus in a mammal, as well as the monitoring of the size, location and number of thrombi in a mammal, as well as dissolution or growth of the thrombus.

In employing the compounds, compositions or diagnostic compositions in vivo by this method, "administering" is accomplished parenterally, in either a systemic or local targeted manner. Systemic administration is accomplished by injecting the compounds, compositions by diagnostic compositions of the present invention into a convenient and accessible vein or artery. This includes but is not limited to administration by the ankecubutal vein. Local targeted administration is accomplished by injecting the compounds, compositions or diagnostic compositions of the present invention proximal in flow to a vein or artery suspected to contain thrombi distal to the injection site. This includes but is not limited to direct injection into the coronary arterial vasculature to image coronary thrombi, into the carotid artery to image thrombi in the cerebral vasculature, or into a pedal vein to image deep vein thrombosis of the leg.

The detecting of a thrombus by imaging is made possible by the presence of radioactive atoms localized at such thrombus.

The radioactive atoms associated with the compositions and diagnostic compositions of the present invention are preferably imaged using a radiation detection means capable of detecting gamma radiation, such as a gamma camera or the like. Typically, radiation imaging cameras employ a conversion medium (wherein the high energy gamma ray is absorbed, displacing an electron which emits a photon upon its return to the orbital state), photoelectric detectors arranged in a spatial detection chamber (to determine the position of the emitted photons), and circuitry to analyze the photons detected in the chamber and produce an image.

The following examples are illustrative, but not limiting, of the method and compositions of the present invention. Other suitable modifications and adaptations of the variety of conditions and parameters normally encountered and obvious to those skilled in the art are within the spirit and scope of the invention.

Scheme 1

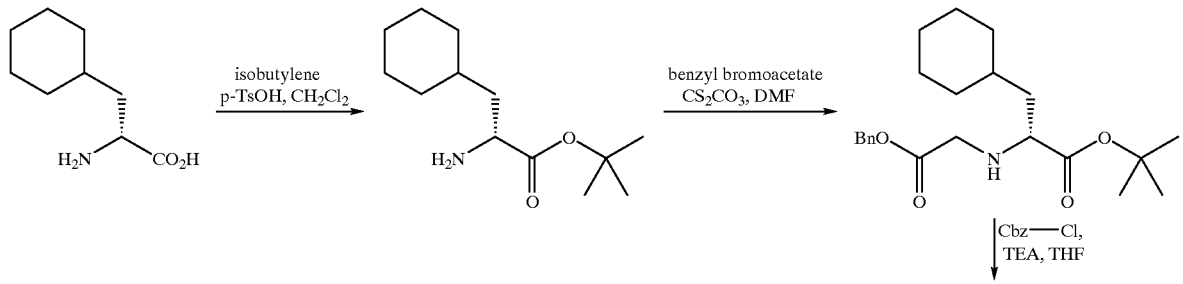

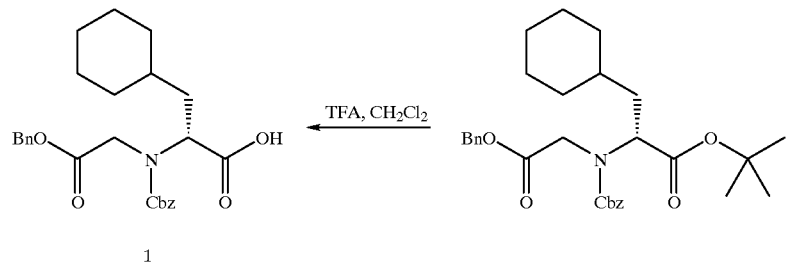
Scheme 2
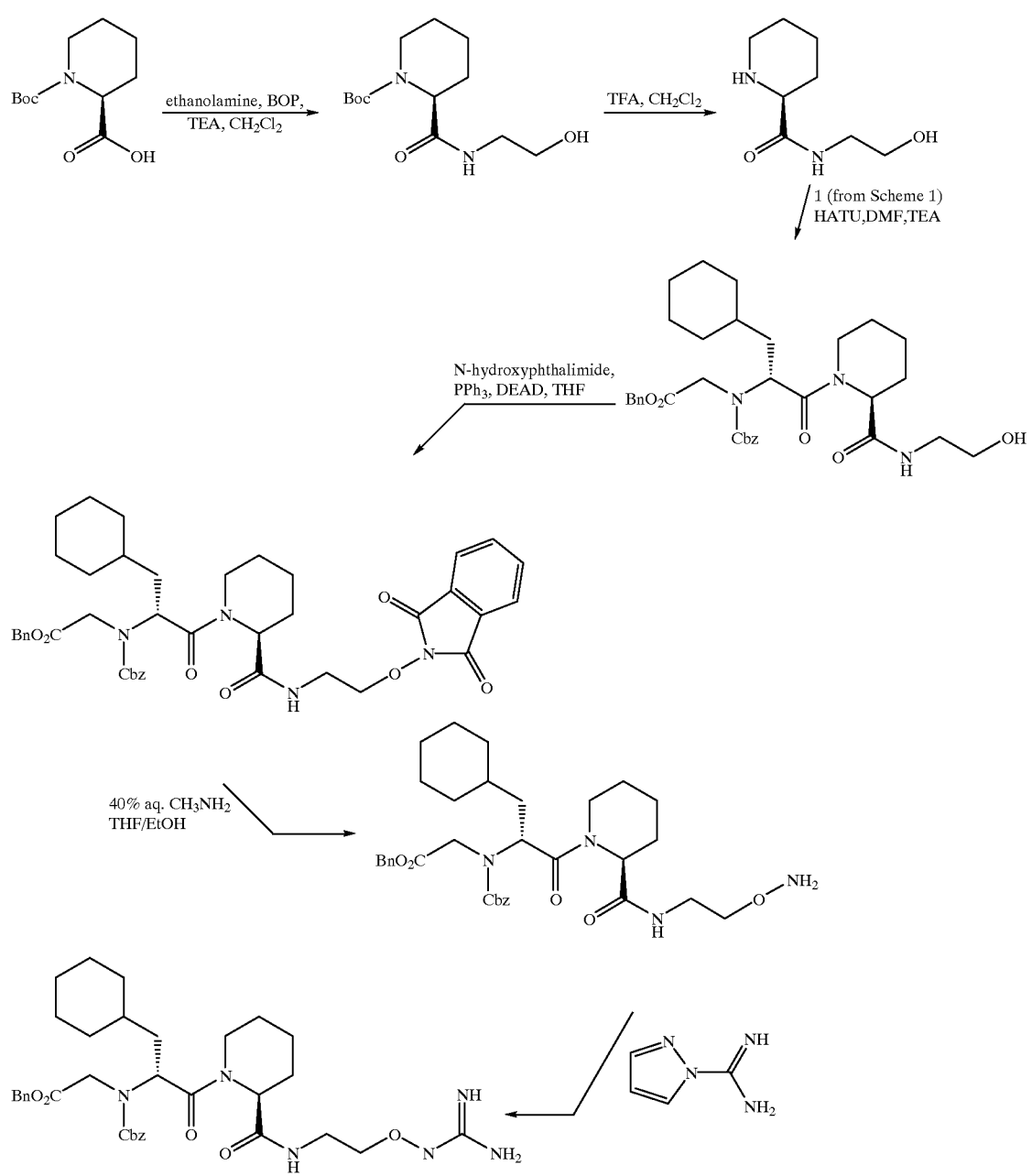

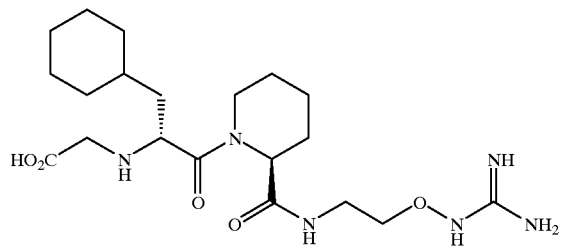
Scheme 3
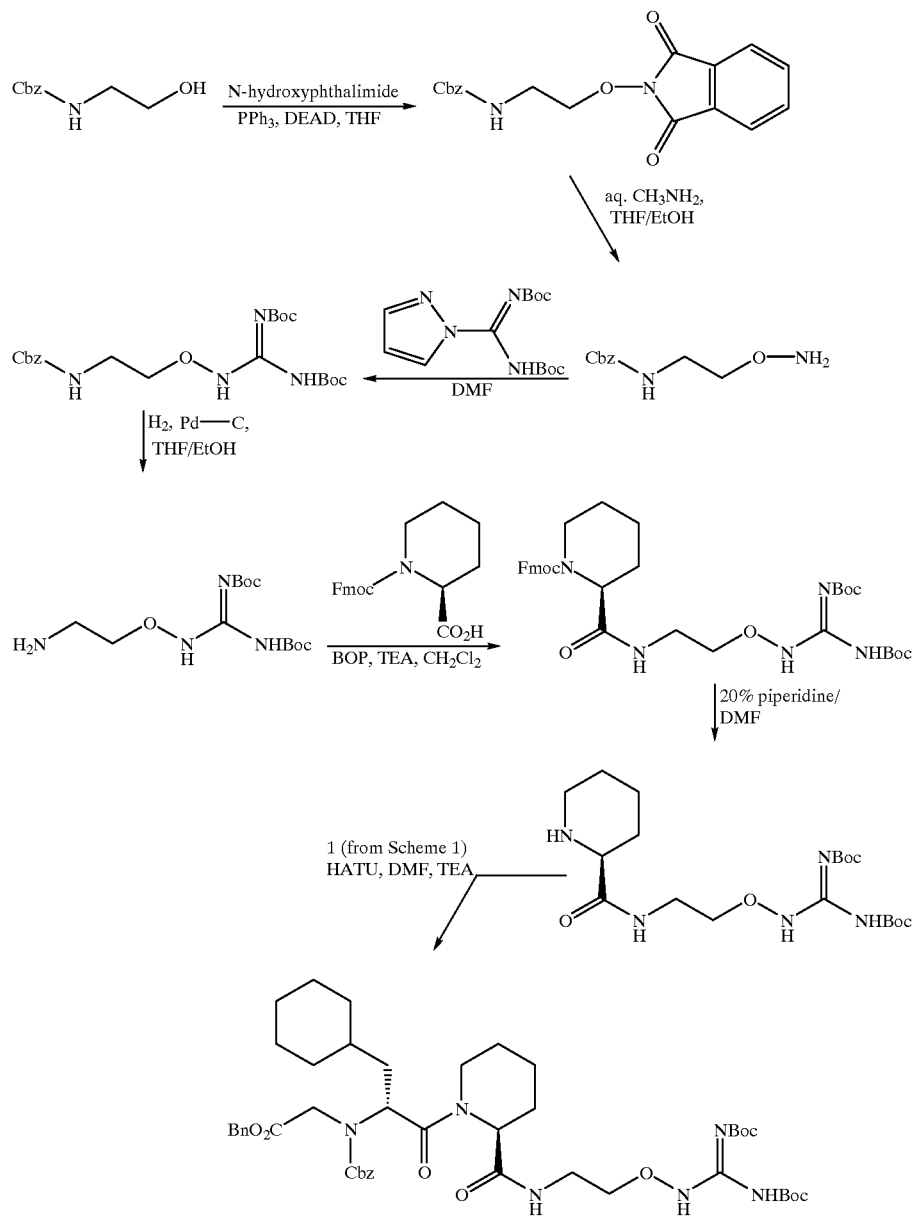

-continued
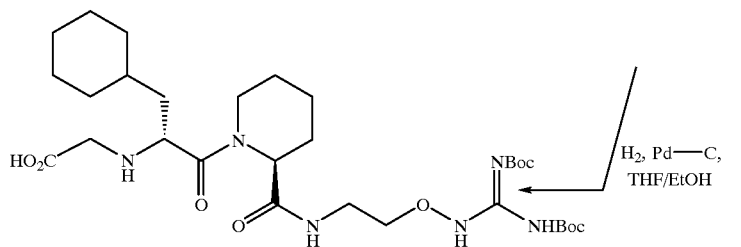
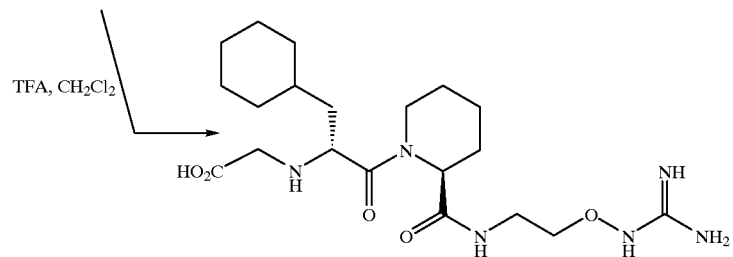
25
Scheme 4
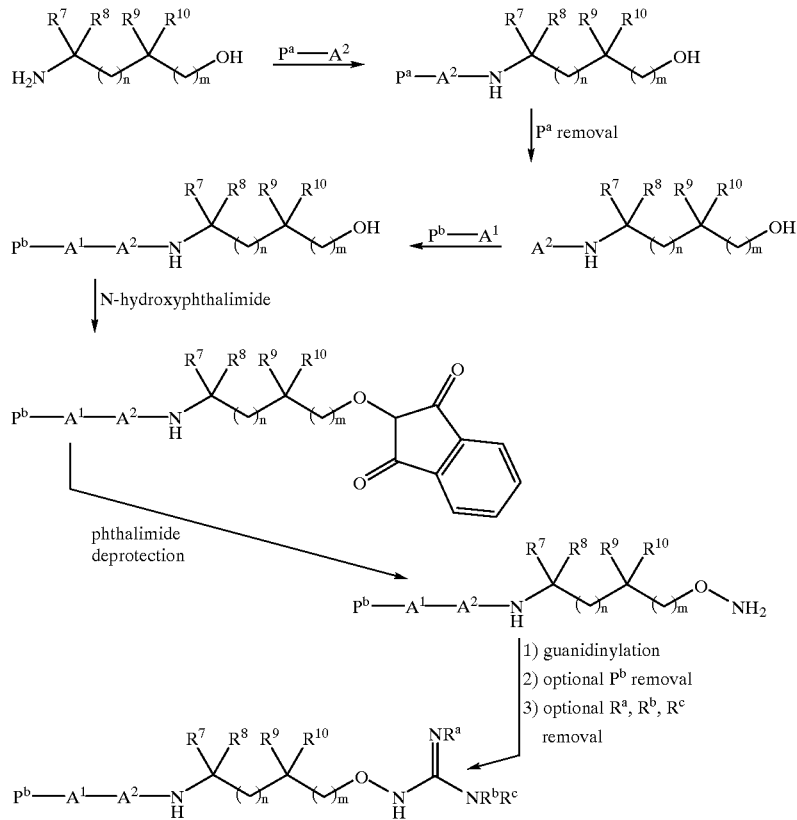

Scheme 5
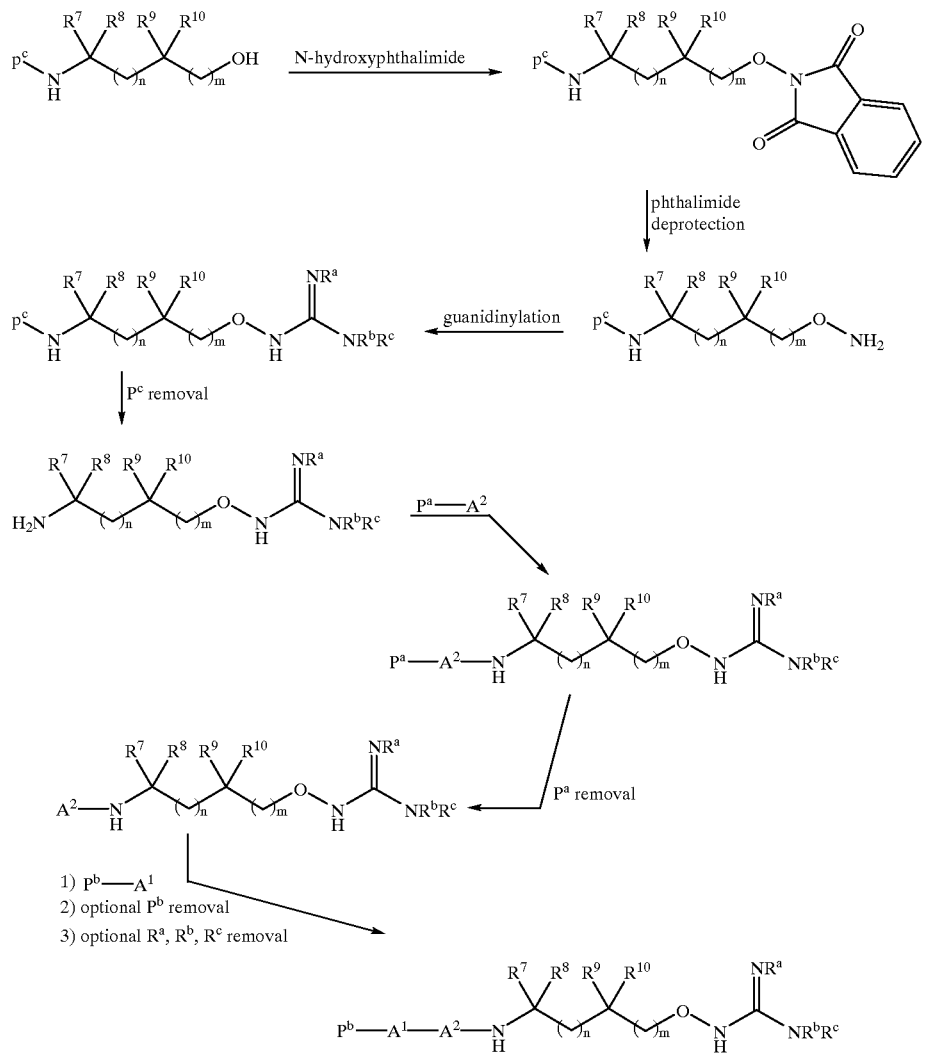
Scheme 6
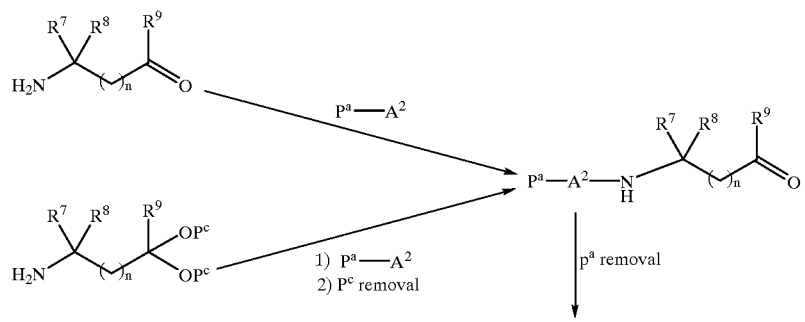

-continued

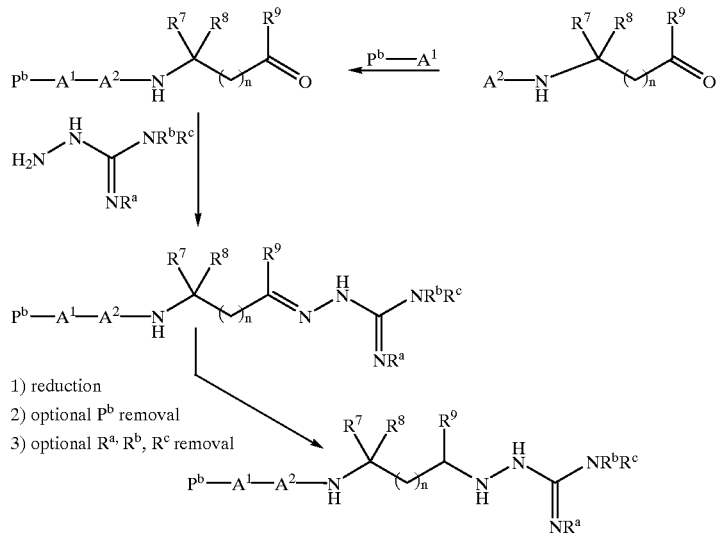

1) reduction
2) optional P^b removal
3) optional R^a, R^b, R^c removal

EXAMPLE 1

HO₂CCH₂—NH—D-Cha-L-Pic-NH(CH₂)₂O—NH—C(=NH)NH₂ di(trifluoroacetate)

Procedure A:

a) D-Cyclohexylalanine Tert-butyl Ester (D-Cha-O-^tBu)

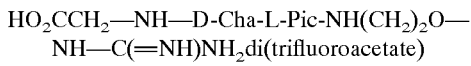

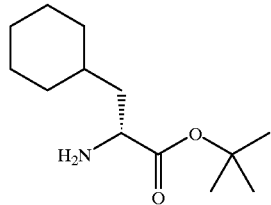

A suspension of D-cyclohexylalanine (1.50 g, 8.77 mmol), p-toluenesulfonic acid monohydrate (6.70 g, 3 5.2 mmol), and 2-methylpropene (ca.

100 mL) in dichloromethane (50 mL) was vigorously stirred in a pressure flask at ambient temperature for 3 days. The resulting homogeneous solution was cooled to −78° C., quenched with aqueous NaHCO₃ (ca. 150 mL), and stirred at ambient temperature for 2.5 h. This was extracted with dichloromethane and the dichloromethane layer was washed with brine, dried over Na₂SO₄, and filtered. The evaporated filtrate was then purified by flash chromatography (ethyl acetate) giving the title compound (1.33 g, 67%) as a pale yellow oil. ¹H NMR (300 MHz, CDCl₃) d 3.37 (dd, 1H, J=8.2 Hz, 5.7 Hz), 1.72 (m, 5H), 1.54 (m, 3H), 1.46 (s, 11H (^tBu+H₂O)), 1.23 (m, 3H), 0.93 (m, 2H).

b) BnO₂CCH₂—D-Cha-O-^tBu

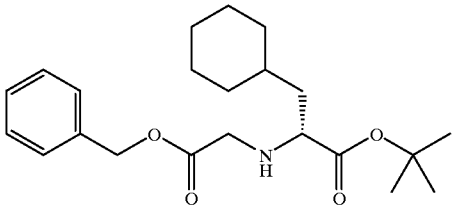

A mixture of the product of the preceding step (1.31 g, 5.76 mmol), benzyl 2-bromoacetate (1.46 g, 6.38 mmol), and cesium carbonate (2.28 g, 7.00 mmol) in N,N-dimethylformamide (ca. 50 mL) was stirred at 60° C. for 4 h. After evaporating the solvent in vacuo, the crude product was dissolved in dichloromethane and filtered. The evaporated filtrate was purified by flash chromatography (5% ethyl acetate in dichloromethane) giving the title compound (1.29 g, 60%) as a pale yellow oil. ¹H NMR (300 MHz, CDCl₃) d 7.35 (m, 5H), 5.16 (s, 2H), 3.42 (dd, 2H, J=30 Hz, 17 Hz), 3.22 (t, 1H, J=6.9 Hz), 1.68 (m, 5H), 1.45 (m, 12H), 1.20 (m, 3H), 0.90 (m, 2H).

c) BnO₂CCH₂—N-Cbz-D-Cha-O-^tBu

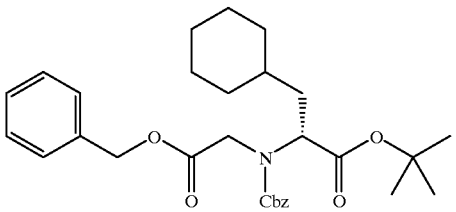

A solution of the product of the preceding step (1.29 g, 3.43 mmol) in anhydrous tetrahydrofuran (50 mL) was reacted portionwise with benzyl chloroformate (3.88 g, 22.8 mmol) and triethylamine (2.18 g, 21.5 mmol) at ambient temperature over 2 days. After evaporating in vacuo, the crude product was dissolved in dichloromethane, washed with dilute aqueous ammonia, pH 7 buffer, and brine, dried over Na₂SO₄, and filtered. The evaporated filtrate was then purified by flash chromatography (20% ethyl acetate in hexanes) giving the title compound (1.30 g, 75%) as a clear oil. This product appeared by proton NMR to be a ca. 1:1 mixture of two rotational isomers. $^1$H NMR (300 MHz, CDCl$_3$) δ 7.32 (m, 10H), 5.20 (s, 1H), 5.17 (s, 1H), 5.09 (s, 1H), 5.05 (s, 1H), 4.90 (dd, 0.5H, J=8.9 Hz, 6.1 Hz), 4.70 (dd, 0.5H, J=8.9 Hz, 6.1 Hz), 4.19 (dd, 1H, J=18 Hz, 7.2 Hz), 3.90 (dd, 1H, J=18 Hz, 8.3 Hz), 1.57 (m, 8H), 1.41 (s, 4.5H), 1.38 (s, 4.5H), 1.14 (m, 3H), 0.88 (m, 2H).

d) BnO$_2$CCH$_2$—N-Cbz-D-Cha-OH (1)

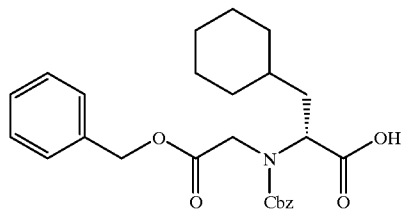

The product of the preceding step (1.28 g, 2.50 mmol) was dissolved in dichloromethane (ca. 15 mL) and treated with neat trifluoroacetc acid (ca. 5 mL) at ambient temperature for 1 hour. After evaporation, the crude product was dissolved in dichloromethane, washed with pH 7 buffer and brine, dried over Na$_2$SO$_4$, filtered and the filtrate evaporated giving the title compound (1.09 g, 96%) as a clear oil that appeared by proton NMR to be a mixture of rotational isomers. $^1$H NMR (300 MHz, CDCl$_3$) δ 7.31 (m, 10H), 5.22 (d, 1H, J=2.1 Hz), 5.19 (d, 1H, J=3.8 Hz), 5.10 (s, 1H), 5.07 (s, 1H), 4.83 (dd, 0.5H, J=9.4 Hz, 5.5 Hz), 4.42 (m, 0.5H), 4.29 (dd, 1H, J=62 Hz, 18 Hz), 3.87 (dd, 1H, J=18 Hz, 4.0 Hz), 1.79 (m, 2H), 1.60 (m, 6H), 1.14 (m, 3H), 0.90 (m, 2H). Mass spectrum (MALDI-TOF, α-cyano-4-hydroxycinnamic acid matrix) calcd. for C$_{26}$H$_{31}$NO$_6$: 476.2 (M+Na). Found: 476.6.

Scheme 1 summarizes steps a through d of Procedure A for forming intermediate BnOOCCH$_2$—N-Cbz-D-Cha-OH (1).

e) N-Boc-L-Pic-NH(CH$_2$)$_2$OH

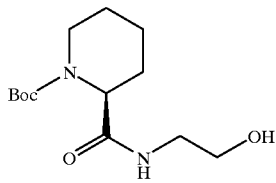

A mixture of N-(tert-butoxycarbonyl)-pipecolinic acid (2.01 g, 8.78 mmol) and ethanolamine (0.59 g, 9.7 mmol) was warmed under a stream of nitrogen and dissolved in anhydrous dichloromethane (ca. 100 mL) and triethylamine (2.5 mL). A solution of benzotriazole-1-yl-oxy-tris-(dimethylamino)-phosphonium hexafluorophosphate (BOP; 3.90 g, 8.81 mmol) in anhydrous dichloromethane (ca. 40 mL) was then added via cannula and the combined mixture stirred at ambient temperature under nitrogen for 3 days. After evaporation the crude product was dissolved in dichloromethane, washed with aqueous NaHCO$_3$ and brine, dried over Na$_2$SO$_4$, and filtered. The evaporated filtrate was then purified by flash chromatography (ethyl acetate) giving the title compound (2.37 g, 99%) as a white solid. $^1$H NMR (300 MHz, CDCl$_3$) δ 6.58 (bs, 1H), 4.74 (bs, 1H), 4.03 (bd, 1H, J=11 Hz), 3.71 (t, 2H, J=4.9 Hz), 3.44 (m, 2H), 3.00 (m, 1H), 2.83 (bt, 1H, J=12 Hz), 2.29 (bd, 1H, J=10 Hz), 1.55 (m, 5H), 1.48 (s, 9H). Mass spectrum (MALDI-TOF, α-cyano-4-hydroxycinnamic acid matrix) calcd. for C$_{13}$H$_{24}$N$_2$O$_4$: 295.2 (M+Na). Found: 295.0.

f) L-Pic-NH(CH$_2$)$_2$OH Trifluoroacetate

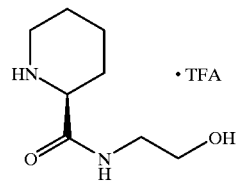

The product of the preceding step (1.54 g, 5.66 mmol) was dissolved in dichloromethane (ca. 15 mL) and reacted with neat trifluoroacetic acid (ca. 5 mL) at ambient temperature for 1.5 hours. The crude product was evaporated and purified by flash chromatography (25% methanol in dichloromethane) giving the title compound (1.64 g, 100%) as a pale yellow gum. $^1$H NMR (300 MHz, CDCl$_3$) δ 3.82 (dd, 1H, J=12 Hz, 3.2 Hz), 3.64 (m, 2H), 3.43 (m, 3H), 3.24 (ddd, 1H, J=14 Hz, 6.4 Hz, 4.1 Hz), 2.98 (td, 1H, J=13 Hz, 3.3 Hz), 2.14 (dd, 1H, J=14 Hz, 3.3 Hz), 1.92 (m, 2H), 1.69 (m, 3H). Mass spectrum (MALDI-TOF, α-cyano-4-hydroxycinnamic acid matrix) calcd. for C$_8$H$_{16}$N$_2$O$_2$: 173.1 (M+H), 195.1 (M+Na). Found: 173.3, 195.3.

g) BnO$_2$CCH$_2$—N-Cbz-D-Cha-L-Pic-NH(CH$_2$)$_2$OH

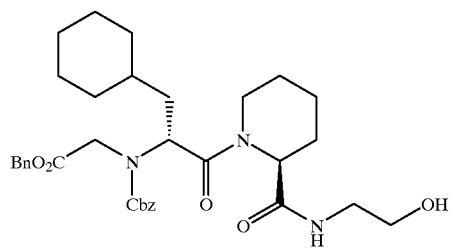

The product of step d (1.07 g, 2.35 mmol) and O-(7-azabenzotriazole-1-yl)-1,1,3,3,-tetramethyluronium hexafluorophosphate (HATU; 1.00 g, 2.63 mmol) were dissolved in N,N-dimethylformamide (ca. 30 mL). To this was added triethylamine (0.66 g, 6.5 mmol) and a solution of the product of step f (1.10 g, 2.75 mmol) in N,N-dimethylformamide (11.0 mL). After stirring under nitrogen at ambient temperature for 3 days, the crude product was evaporated in vacuo and dissolved in dichloromethane. This solution was washed with aqueous NaHCO$_3$, pH 7 buffer and brine, dried over Na$_2$SO$_4$, and filtered. The evaporated filtrate was then purified by flash chromatography (50% ethyl acetate in dichloromethane) giving the title compound (1.08 g, 75%) as a clear oil. $^1$H NMR (300 MHz, CDCl$_3$) δ 7.33 (m, 7H), 7.23 (m, 3H), 7.04 (bt, 1H, J=6 Hz), 5.39 (t, 1H, J=7.5 Hz), 5.22 (bd, 1H, J=6 Hz), 5.15 (d, 1H, J=4.2 Hz), 5.10 (d, 1H, J=7.3 Hz), 5.03 (s, 2H), 4.33 (bd, 1H, J=14 Hz), 4.15 (d, 2H, J=3.8 Hz), 3.68 (m, 2H), 3.40 (m, 3H), 3.09 (m, 1H), 2.47 (bd, 1H, J=14 Hz), 1.64 (m, 12H), 1.43 (m, 2H), 1.15 (m, 5H), 0.94 (m, 2H). Mass spectrum (MALDI-TOF, α-cyano-4-hydroxycinnamic acid matrix) calcd. for C$_{34}$H$_{45}$N$_3$O$_7$: 630.3 (M+Na). Found: 630.8.

h) BnO$_2$CCH$_2$—N-Cbz-D-Cha-L-Pic-NH(CH$_2$)$_2$O-Phthalimide

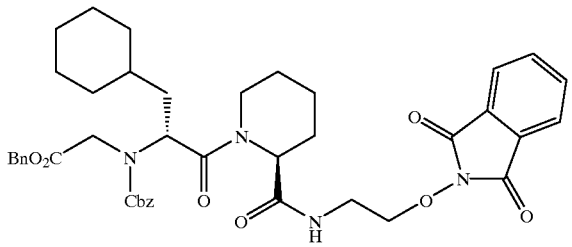

A mixture of the product of the preceding step (1.05 g, 1.73 mmol), N-hydroxyphthalimide (0.290 g, 1.78 mmol), and triphenylphosphine (0.469 g, 1.79 mmol) were warmed under a stream of nitrogen and dissolved in anhydrous tetrahydrofuran (ca. 40 mL). Diethylazadicarboxylate (0.332 g, 1.91 mmol) was added via syringe and the reaction was stirred under nitrogen at ambient temperature for 18 hours. After evaporation, the crude product was purified by flash chromatography (25% ethyl acetate in dichloromethane) giving the title compound (0.965 g, 74%) as a white solid. $^1$H NMR (300 MHz, CDCl$_3$) δ 7.73 (m, 4H), 7.23 (m, 10H), 5.39 (t, 1H, J=7.4 Hz), 5.22 (m, 1H), 5.06 (m, 4H), 4.22 (m, 4H), 3.68 (m, 1H), 3.44 (m, 1H), 3.22 (m, 1H), 2.45 (bd, 1H, J=13 Hz), 1.52 (m, 14H), 1.14 (m, 5H), 0.90 (m, 2H). Mass spectrum (MALDI-TOF, α-cyano-4-hydroxycinnamic acid matrix) calcd. for C$_{42}$H$_{48}$N$_4$O$_9$: 775.3 (M+Na). Found: 775.9.

i) BnO$_2$CCH$_2$—N-Cbz-D-Cha-L-Pic-NH(CH$_2$)$_2$O—NH$_2$

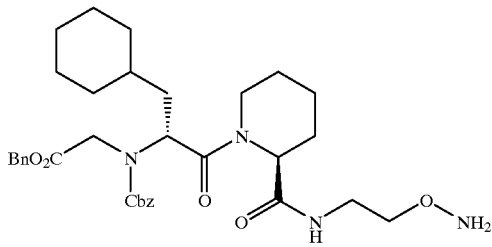

The product of the preceding step (0.950 g, 1.26 mmol) was dissolved in a 1:1 mixture of tetrahydrofuran and ethanol (ca. 20 mL) and reacted with a 40% aqueous solution of methylamine (ca. 10 mL) at ambient temperature for 1 hour. After evaporation in vacuo, the crude product was dissolved in ethyl acetate and filtered. The evaporated filtrate was then purified by flash chromatography (5% methanol in dichloromethane) giving the title compound (0.674 g, 86%) as a pale yellow oil. $^1$H NMR (300 MHz, CDCl$_3$) δ 7.33 (m, 7H), 7.23 (m, 3H), 6.96 (m, 1H), 5.49 (m, 1H), 5.40 (t, 1H, J=7.5 Hz), 5.15 (m, 5H), 4.29 (bd, 1H, J=13 Hz), 4.15 (m, 2H), 3.66 (m, 3H), 3.29 (m, 1H), 3.12 (m, 1H), 2.46 (m, 1H), 1.65 (m, 12H), 1.36 (m, 2H), 1.18 (m, 5H), 0.92 (m, 2H). Mass spectrum (MALDI-TOF, α-cyano-4-hydroxycinnamic acid matrix) calcd. for C$_{34}$H$_{46}$N$_4$O$_7$: 645.3 (M+Na). Found: 645.7.

j) BnO$_2$CCH$_2$—N-Cbz-D-Cha-L-Pic-NH(CH$_2$)$_2$O—NH—C(=NH)NH$_2$

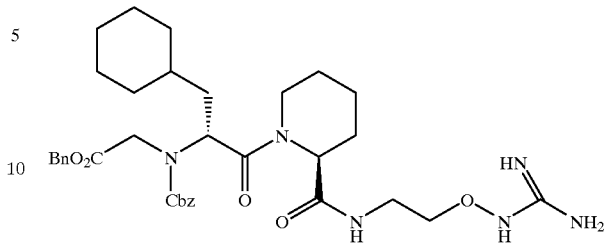

A mixture of the product of the preceding step (0.654 g, 1.05 mmol), 1-H-pyrazolecarboxamidine hydrochloride (0.771 g, 5.26 mmol), and N,N-diisopropylethylamine (0.74 g, 5.8 mmol) was stirred in N,N-dimethylformamide (ca. 15 mL) at 55° C. for 2 days. After evaporating in vacuo, the crude product was dissolved in dichloromethane, washed with aqueous NaHCO$_3$, pH 7 buffer and brine, dried over Na$_2$SO$_4$, and filtered. The evaporated filtrate was then purified by flash chromatography (12% methanol in dichloromethane) giving the title compound (0.275 g, 39%) as a white solid. $^1$H NMR (300 MHz, CDCl$_3$) δ 7.33 (m, 6H), 7.24 (m, 4H), 5.38 (t, 1H, J=7.5 Hz), 5.14 (m, 5H), 4.14 (m, 3H), 3.90 (m, 2H), 3.61 (m, 1H), 3.32 (m, 1H), 3.11 (m, 1H), 2.44 (m, 1H), 1.63 (m, 12H), 1.40 (m, 2H), 1.16 (m, 5H), 0.92 (m, 2H). Mass spectrum (MALDI-TOF, α-cyano-4-hydroxycinnamic acid matrix) calcd. for C$_{35}$H$_{48}$N$_6$O$_7$: 665.4 (M+H), 687.3 (M+Na). Found: 665.7, 688.1.

k) HO$_2$CCH$_2$—NH—D-Cha-L-Pic-NH(CH$_2$)$_2$O—NH—C(=NH)NH$_2$di(trifluoroacetate)

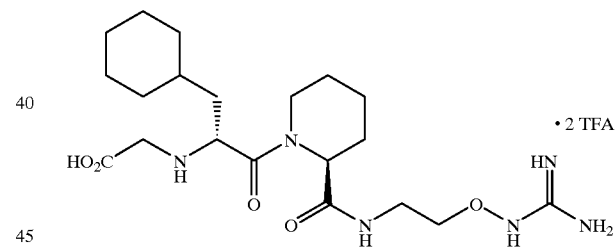

The product of the preceding step (0.166 g, 0.250 mmol) and 10% palladium(0) on activated carbon (ca. 0.010 g) were stirred in a degassed 4:1 mixture of ethanol and tetrahydrofuran (ca. 50 mL) under hydrogen, at ambient temperature, for 3 hours. After filtering over Celite and evaporating, the crude product was triturated with diethyl ether, dissolved in dichloromethane, filtered and evaporated. This was then purified by reverse-phase HPLC (methanol/water/TFA eluent), evaporated in vacuo, and triturated again with diethyl ether giving the title compound (0.034 g, 20%) as a white solid. $^1$H NMR (300 MHz, CDCl$_3$/CD$_3$OD) δ 5.26 (bs, 1H), 3.87 (m, 4H), 3.64 (m, 1H), 3.44 (m, 1H), 3.18 (m, 2H), 2.46 (m, 1H), 1.72 (m, 8H), 1.37 (m, 6H), 1.22 (m, 5H), 0.95 (m, 2H). Mass spectrum (MALDI-TOF, α-cyano-4-hydroxycinnamic acid matrix) calcd. for C$_{20}$H$_{36}$N$_6$O$_5$: 441.3 (M+H), 463.3 (M+Na). Found: 441.6, 463.6.

Scheme 2 summarizes steps e through k of Procedure A for forming HOOC—CH$_2$—NH—D-Cha-L-Pic-NH(CH$_2$)$_2$O—NH—C(=NH)NH$_2$di(trifluoroacetate).

Procedure B:
a) N-[2-(Benzyloxycarbonylamino)ethoxy]phthalimide

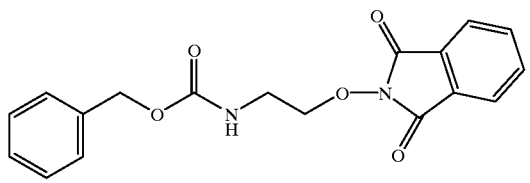

To a solution of benzyl N-(2-hydroxyethyl)carbamate (5.9 g, 30 mmol), N-hydroxyphthalimide (4.9 g, 30 mmol), triphenylphosphine (7.9 g, 30 mmol) in tetrahydrofuran (100 mL) was added diethyl azodicaroxylate (5.2 g, 30 mmol). The reaction mixture was stirred at room temperature overnight. Ethyl acetate (200 mL) was added and the solution was washed with saturated NaHCO$_3$ (2×100 mL) and brine (100 mL), dried over Na$_2$SO$_4$, and filtered. The evaporated filtrate was purified by flash chromatography (0–4% ethyl acetate in dichloromethane) giving the title compound as a white solid (9.3 g, 91%). $^1$H-NMR (300 MHz, CDCl$_3$) δ 7.84 (m, 2H), 7.78 (m, 2H), 7.37 (m, 5H), 5.97 (bs, 1H), 5.14 (s, 2H), 4.27 (t, J=4.9 Hz, 2H), 3.51 (q, J=5.2 Hz, 2H).

b) 2-(Benzyloxycarbonylamino)ethoxyamine

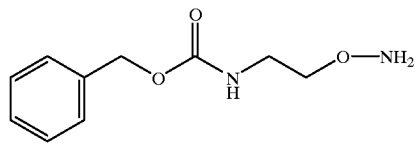

To a solution of N-[2-(benzyloxycarbonylamino)ethoxy]phthalimide (1.36 g, 4.00 mmol), as prepared in the preceding step, in ethanol (20 mL) and tetrahydrofuran (20 mL) was added 40% methylamine (2.0 mL, 25 mmol) and the reaction was stirred at ambient temperature for 1 h. After evaporating the solvent, the residue was purified by flash column chromatography (75–100% ethyl acetate in hexanes) to give the title compound as a white solid (0.80 g, 95%). $^1$H-NMR (300 MHz, CDCl$_3$) δ 7.36 (m, 5H), 5.47 (bs, 2H), 5.21 (bs, 1H), 5.10 (s, 2H), 3.72 (t, J=5.0 Hz, 2H), 3.44 (q, J=5.0 Hz, 2H).

c) [N,N'-Di(tert-butoxycarbonyl)]-2-(benzyloxycarbonylamino)ethoxyguanidine

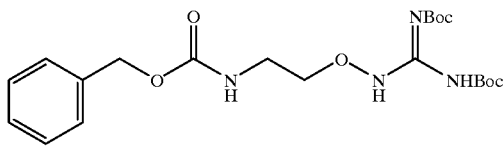

To a solution of 2-(benzyloxycarbonylamino)ethoxyamine (0.78 g, 3.70 mmol), as prepared in the preceding step, in N,N-dimethylformamide (20 mL) was added [N,N'-di(tert-butoxycarbonyl)]amidinopyrazole (1.25 g, 4.00 mmol). The mixture was stirred at ambient temperature overnight, the solvent was evaporated in high vacuum. The residue was purified by flash column chromatography (0–5% ethyl acetate in dichloromethane) to give the title compound as a colorless oil (1.55 g, 93%). $^1$H-NMR (300 MHz, CDCl$_3$) δ 9.08 (s, 1H), 7.67 (s, 1H), 7.33 (m, 5H), 6.21 (bs, 1H), 5.21 (bs, 1H), 5.11 (s, 2H), 4.12 (t, J=4.8 Hz, 2H), 3.54 (q, J=4.9 Hz, 2H), 1.49 (s, 9H), 1.46 (s, 9H).

d) [N,N'-Di(tert-butoxycarbonyl)]2-aminoethoxyguanidine

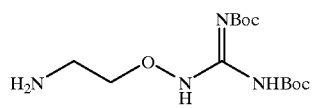

A mixture of [N,N'-di(tert-butoxycarbonyl)]2-(benzyloxycarbonylamino)ethoxyguanidine (0.73 g, 1.50 mmol), as prepared in the preceding step, 10% Pd/C (0.07 g) in ethanol (20 mL) and tetrahydrofuran (20 mL) was stirred under hydrogen (balloon) for 30 min. The catalysts were removed by filtration through Celite, the filtrate was concentrated in vacuo, and the residue was purified on a Waters silica Sep-Pak (5% methanol in dichloromethane saturated with ammonia) to give the title compound as a colorless oil (0.29 g, 61%). $^1$H-NMR (300 MHz, CDCl$_3$) δ 9.08 (bs, 1H), 4.08 (t, J=5.2 Hz, 2H), 2.99 (q, J=5.1 Hz, 2H), 1.50 (s, 9H), 1.48 (s, 9H).

e) Fmoc-L-Pic-NH(CH$_2$)$_2$O—NH—C(=NBoc)NHBoc

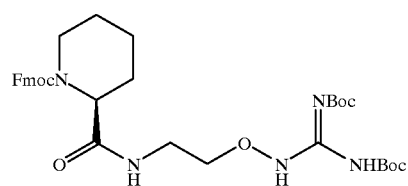

[N,N'-Di(tert-butoxycarbonyl)]2-aminoethoxyguanidine (1.33 g, 4.17 mmol), as prepared in the preceding step, and Fmoc-pipecolinic acid (1.46 g, 4.17 mmol) were warmed under a stream of nitrogen and dissolved in dry dichloromethane (50 mL) and triethylamine (1.5 mL). A solution of BOP reagent(1.86 g, 4.20 mmol) in dry dichloromethane (50 mL) was added to the above solution via cannula and the resulting mixture was stirred 18 hours at ambient temperature. After evaporation, the crude product was purified by flash chromatography (33% hexanes in ethyl acetate) giving the title compound as a white solid (2.65 g, 98%). $^1$H NMR (300 MHz, CDCl$_3$) δ 9.12 (s, 1H), 7.77 (s, 1H), 7.74 (s, 1H), 7.38 (m, 8H), 4.85 (m, 1H), 4.41 (bs, 2H), 4.27 (m, 1H), 4.11 (m, 3H), 3.59 (m, 2H), 3.23 (m, 1H), 2.30 (bd, 1H, J=13 Hz), 1.83 (m, 2H), 1.66 (m, 3H), 1.48 (s, 9H), 1.47 (m, 9H).

f) H-L-Pic-NH(CH$_2$)$_2$O—NH—C(=NBoc)NHBoc

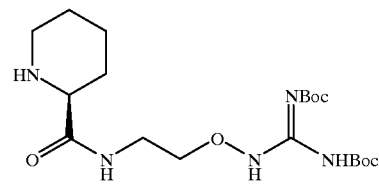

The product of the preceding step (2.63 g, 4.04 mmol) was stirred in a solution of 20% piperidine in N,N-dimethylformamide (50 mL) at ambient temperature for 18 hours. After evaporating the solvents in vacuo at 55° C., the crude product was dissolved in dichloromethane, washed with pH 7 buffer and brine, dried over Na$_2$SO$_4$, and filtered. The evaporated filtrate was purified by flash chromatography (15% methanol in dichloromethane) giving the title compound as a white solid (1.03 g, 60%). $^1$H NMR (300 MHz, CDCl$_3$) δ 9.17 (bs, 1H), 7.72 (bs, 1H), 7.61 (m, 1H), 4.11 (t, 2H, J=4.7 Hz), 3.58 (m, 2H), 3.29 (dd, 1H, J=10.2 Hz, 3.2 Hz), 3.12 (m, 1H), 2.67 (m, 1H), 1.99 (m, 4H), 1.82

(m, 1H), 1.57 (m, 1H), 1.51 (s, 9H), 1.50 (s, 9H), 1.42 (m, 3H). Mass spectrum (MALDI-TOF, α-cyano-4-hydroxycinnamic acid matrix) calcd. for $C_{19}H_{35}N_5O_6$: 230.2 (M-2 Boc+H). Found: 230.7.

g) BnO$_2$CCH$_2$—N-Cbz-D-Cha-L-Pic-NH(CH$_2$)$_2$O—NH—C(=NBoc)NHBoc

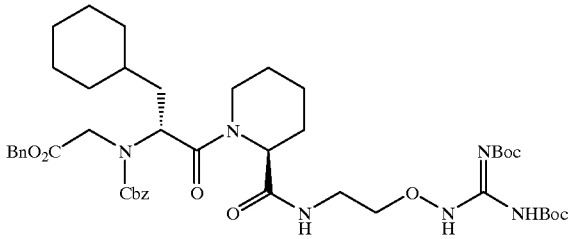

The product of the preceding step (0.91 g, 2.11 mmol) and HATU (1.00 g, 2.63 mmol) were dissolved in dry N,N-dimethylformamide (50 mL) under nitrogen and reacted with a solution of the product of Example 1, Procedure A, step d (1.10 g, 2.43 mmol) in N,N-dimethylformamide (11 mL) via syringe. Triethylamine (1.0 mL, 7.2 mmol) was then added and the reaction was stirred at ambient temperature under nitrogen for 18 hours. After evaporating the solvent in vacuo, the crude product was purified by flash chromatography (40% hexanes in ethyl acetate) giving the title compound as a white solid (1.74 g, 95%). $^1$H NMR (300 MHz, CDCl$_3$) δ 9.13 (s, 1H), 8.05 (s, 1H), 7.25 (m, 10H), 7.09 (t, 1H, J=5.6 Hz), 5.15 (m, 5H), 4.16 (m, 4H), 3.66 (m, 1H), 3.25 (dd, 1H, J=14Hz, 5.2 Hz), 3.09 (m, 1H), 2.46 (bd, 1H, J=12 Hz), 1.58 (m, 13H (alkyl+H$_2$O)), 1.46 (s, 9H), 1.43 (s, 9H), 1.13 (m, 7H), 0.89 (m, 4H). Mass spectrum (MALDI-TOF, gentisic acid matrix) calcd. for $C_{45}H_{64}N_6O_{11}$: 887.5 (M+Na), 665.4 (M-2 Boc+H). Found: 887.8, 665.5.

h) HO$_2$CCH$_2$—NH—D-Cha-L-Pic-NH(CH$_2$)$_2$O—NH—C(=NBoc)NHBoc

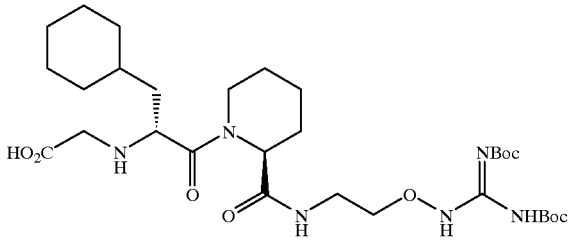

The product of the preceding step (1.38 g, 1.59 mmol) and 10% palladium on carbon (0.16 g) were stirred in 1:1 ethanol/tetrahydrofuran (100 mL) under hydrogen for 6 hours at ambient temperature. After filtering the reaction over Celite, the filtrate was evaporated and the crude product purified by flash chromatography (20% methanol in dichloromethane) giving the title compound as an off-white solid (0.67 g, 66%). $^1$H NMR (300 MHz, CDCl$_3$) δ 9.16 (bs, 1H), 7.85 (bs, 1H), 7.74 (bs, 1H), 5.26 (bs, 2H), 4.10 (m, 2H), 3.82 (bd, 1H, J=12 Hz), 3.52 (m, 6H), 2.85 (bd, 2H, J=16 Hz), 2.38 (m, 1H), 1.63 (m, 14H), 1.46 (m, 21H), 1.25 (m, 4H), 0.94 (m, 2H).

i) HO$_2$CCH$_2$—NH—D-Cha-L-Pic-NH(CH$_2$)$_2$O—NH—C(=NH)NH$_2$di(trifluoroacetate)

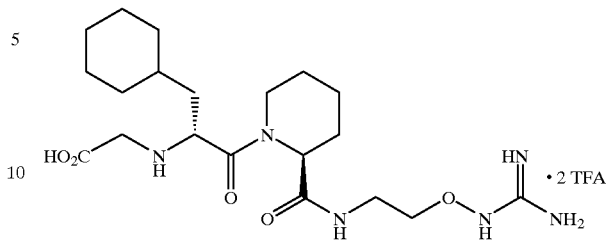

The product of the preceding step (0.67 g, 1.05 mmol) was dissolved in methylene chloride (10 mL) and reacted with trifluoroacetic acid (15 mL) for 22 hours at ambient temperature. After thoroughly evaporating in vacuo at 60° C., the crude product was purified by flash chromatography on standard silica gel (10–30% methanol in dichloromethane with 1% v/v trifluoroacetic acid) giving a pale yellow oil. This was lyophilised 3 times from 1:1 cetonitrile/water (10 mL) giving the title compound as an amorphous white solid (0.63 g, 90%). RP-HPLC shows 98.6% purity (5–100% acetonitrile/water with 0.1% trifluoroacetic acid). $^1$H NMR (300 MHz, CD$_3$OD) δ 5.10 (bs, 1H), 4.15 (s, 1H), 3.95 (m, 3H), 3.60 (t, 2H, J=6.0 Hz), 3.53 (t, 2H, J=5.2 Hz), 3.36 (m, 1H), 2.25 (m, 1H), 1.75 (m, 14H), 1.48 (m, 3H), 1.25 (m, 4H), 1.04 (m, 2H). Mass spectrum (MALDI-TOF, gentisic acid matrix) calcd. for $C_{20}H_{36}N_6O_5$: 463.3 (M+Na), 441.3 (M+H). Found: 463.3, 441.2.

Scheme 3 depicts steps a through i of Procedure B for forming HOOC—CH$_2$—NH—D-Cha-L-Pic-NH(CH$_2$)$_2$O—NH—C(=NH)NH$_2$di(trifluoroacetate).

EXAMPLE 2

HO$_2$CCH$_2$—NH—L-Cha-L-Pic-NH(CH$_2$)$_2$O—NH—C(=NH)NH$_2$ a) L-Cyclohexylalanine tert-butyl ester (L-Cha-O-$^t$Bu)

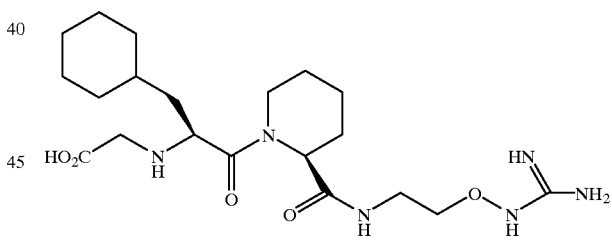

The title compound was prepared from L-cyclohexylalanine hydrochloride (0.92 g, 4.42 mmol) in a manner analogous to Example 1, Procedure A, step a, as a pale gold oil (0.78 g, 78%). $^1$H NMR (300 MHz, CDCl$_3$) δ 3.37 (dd, 1H, J=8.2 Hz, 5.7 Hz), 1.77–1.63 (m, 4H), 1.58–1.49 (m, 3H), 1.46 (s, 9H), 1.44–1.31 (m, 1H), 1.27–1.16 (m, 3H), 0.99–0.84 (m, 2H).

b) BnO$_2$CCH$_2$—L-Cha-O-$^t$Bu

The title compound was prepared from the product of the preceding step (0.74 g, 3.27 mmol) in a manner analogous to Example 1, Procedure A, step b, as a yellow oil (0.82 g, 66%). $^1$H NMR (300 MHz, CDCl$_3$) δ 7.35 (m, 5H), 5.16 (s, 2H), 3.42 (dd, 2H, J=30 Hz, 17 Hz), 3.22 (t, 1H, J=7 Hz), 1.80–1.63 (m, 7H), 1.50–1.38 (m, 12H), 1.25–1.15 (m, 3H), 0.94–0.87 (m, 2H).

c) BnO$_2$CCH—N-Cbz-L-Cha-O-$^t$Bu

The title compound was prepared from the product of the preceding step (0.80 g, 2.13 mmol) in a manner analogous to Example 1, Procedure A, step c, as a yellow oil (0.84 g, 78%). Proton NMR showed the product to be a mixture of two rotational isomers. $^1$H NMR (300 MHz, CDCl$_3$) δ 7.35–7.23 (m, 10H), 5.20 (s, 1H), 5.17 (s, 1H), 5.09 (s, 1H), 5.05 (s, 1H), 4.90 (dd, 0.5H, J=9 Hz, 6 Hz), 4.70 (dd, 0.5H, J=9 Hz, 6 Hz), 4.20 (dd, 1H, J=18 Hz, 7 Hz), 3.90 (dd, 1H, J=18 Hz, 8 Hz), 1.71–1.44 (m, 7H), 1.41 (s, 4.5H), 1.38 (s, 4.5H), 1.20–1.09 (m, 3H), 0.92–0.81 (m, 2H).

d) BnO$_2$CCH$_2$—N-Cbz-L-Cha-OH

The title compound was prepared from the product of the preceding step (0.78 g, 1.53 mmol) in a manner analogous to Example 1, Procedure A, step d, as a pale yellow oil (0.69 g, 100%). Mass spectrum (MALDI-TOF, α-cyano-4-hydroxycinnamic acid matrix) calcd. for C$_{26}$H$_{31}$NO$_6$: 476.2 (M+Na). Found: 476.4.

e) BnO$_2$CCH$_2$—N-Cbz-L-Cha-L-Pic-NH(CH$_2$)$_2$OH

The title compound was prepared from the product of the preceding step (0.66 g, 1.46 mmol) in a manner analogous to Example 1, Procedure A, step g, as a pale yellow oil (0.67 g, 75%). Mass spectrum (MALDI-TOF, α-cyano-4-hydroxycinnamic acid matrix) calcd. for C$_{34}$H$_{45}$N$_3$O$_7$: 630.3 (M+Na). Found: 630.7.

f) BnO$_2$CCH$_2$—N-Cbz-L-Cha-L-Pic-NH(CH$_2$)$_2$O—NPhthalimide

The title compound was prepared from the product of the preceding step (0.14 g, 0.22 mmol) in a manner analogous to Example 1, Procedure A, step h, as a white solid (0.16 g, 96%). Mass spectrum (MALDI-TOF, α-cyano-4-hydroxycinnamic acid matrix) calcd. for C$_{42}$H$_{48}$N$_4$O$_9$: 775.3 (M+Na). Found: 775.8.

g) BnO$_2$CCH$_2$—N-Cbz-L-Cha-L-Pic-NH(CH$_2$)$_2$O—NH$_2$

The title compound was prepared from the product of the preceding step (0.15 g, 0.20 mmol) in a manner analogous to Example 1, Procedure A, step i, as a clear oil (0.11 g, 85%). Mass spectrum (MALDI-TOF, α-cyano-4-hydroxycinnamic acid matrix) calcd. for C$_{34}$H$_{46}$N$_4$O$_7$: 645.3 (M+Na). Found: 646.3.

h) BnO$_2$CCH$_2$—N-Cbz-L-Cha-L-Pic-NH(CH$_2$)$_2$O—NHC(=NH)NH$_2$

The title compound was prepared from the product of the preceding step (0.10 g, 0.17 mmol) in a manner analogous to Example 1, Procedure A, step j, as a clear oil (0.03 g, 25%). Mass spectrum (MALDI-TOF, αcyano-4-hydroxycinnamic acid matrix) calcd. for C$_{35}$H$_{48}$N$_6$O$_7$: 687.3 (M+Na). Found: 688.2.

i) HO$_2$CCH$_2$—NH—L-Cha-L-Pic-NH(CH$_2$)$_2$O—NH—C(=NH)NH$_2$

The product of the preceding step (0.03 g, 0.04 mmol) and 10% palladium (0) on carbon (0.01 g) were dissolved in 1:1 ethanol/tetrahydrofuran, degassed with nitrogen gas then aspirator pressure, and stirred under hydrogen gas at ambient temperature for 6 h. The reaction mixture was filtered over a bed of Celite, the Celite washed with ethanol, tetrahydrofuran, and methanol, and the filtrate evaporated in vacuo. The residue was then triturated with diethyl ether, dissolved in methanol, filtered, and the filtrate evaporated in vacuo giving the title compound as a pale yellow solid (0.01 g, 59%). $^1$H NMR (300 MHz, CD$_3$OD) δ 5.16 (bm, 1H), 4.50 (bd, 1H, J=11 Hz), 4.04 (m, 1H), 3.89 (m, 2H), 3.80 (t, 1H, J=5 Hz), 3.59 (m, 1H), 3.38 (m, 2H), 3.21 (bm, 1H), 3.15 (bs, 2H), 2.75 (m, 0.5H), 2.36 (bd, 0.5H, J=10 Hz), 2.14 (bd, 1H, J=10 Hz), 1.58–1.40 (m, 8H) 1.34–1.15 (m, 6H), 0.95 (m, 3H). Mass spectrum (MALDI-TOF, α-cyano-4-hydroxycinnamic acid matrix) calcd. for C$_{20}$H$_{36}$N$_6$O$_5$: 441.3 (M+H), 463.3 (M+Na), 486.3 (M+K). Found: 441.9, 463.8, 486.1.

EXAMPLE 3

9-Hydroxy-9-fluorenylcarbonyl-L-Pro-NH(CH$_2$)$_2$O—NH—C(=NH)NH$_2$ trifluoroacetate a) Fmoc-L-Pro-NH(CH$_2$)$_2$O—NH—C(=NBoc)NHBoc

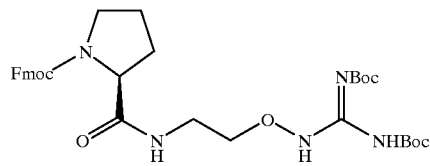

To a mixture of the product of Example 1, Procedure B, step d (0.39 g, 1.22 mmol), Fmoc-proline (0.41 g, 1.22 mmol), and BOP (0.62 g, 1.40 mmol) in anhydrous dichloromethane (40 mL) was added triethylamine (0.5 mL, 3.6 mmol). The reaction stirred at ambient temperature for 16 h, the volatiles evaporated in vacuo, and the residue dissolved in dichloromethane. This solution was washed with pH 7 buffer and brine, dried over Na$_2$SO$_4$ and filtered. The evaporated filtrate was purified by flash chromatography (5% methanol in dichloromethane) giving the title compound as a white solid (0.69 g, 88%). Mass spectrum (MALDI-TOF, αcyano-4-hydroxycinnamic acid matrix) calcd. for C$_{33}$H$_{43}$N$_5$O$_8$: 438.2 (M-2 Boc+H). Found: 438.4.

b) L-Pro-NH(CH$_2$)$_2$O—NH—C(=NBoc)NHBoc

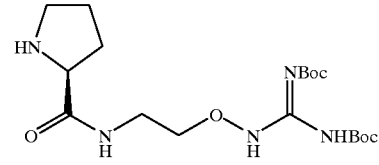

The title compound was prepared from the product of the preceding step (0.67 g, 1.06 mmol) in a manner analogous to Example 1, Procedure B, step f, as a white solid (0.35 g, 78%). Mass spectrum (MALDI-TOF, α-cyano-4-hydroxycinnamic acid matrix) calcd. for C$_{18}$H$_{33}$N$_5$O$_6$: 416.3 (M+H), 216.1 (M-2 Boc+H). Found: 414.8, 215.4.

c) 9-Hydroxy-9-fluorenylcarbonyl-L-Pro-NH(CH$_2$)$_2$O—NH—C(=NBoc)NHBoc

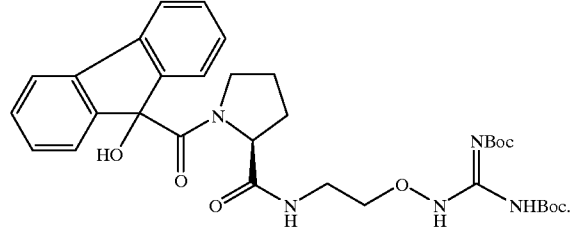

The product of the preceding step (0.34 g, 0.81 mmol), 9-hydroxy-9-fluorenylcarboxylic acid (0.20 g, 0.89 mmol), and BOP (0.47 g, 1.06 mmol) were dissolved in anhydrous dichloromethane (30 mL) and reacted with triethylamine (0.30 mL, 2.15 mmol). After stirring 16 h at ambient temperature, the reaction was evaporated in vacuo and the residue purified by flash chromatography (10% methanol in dichloromethane) giving the title compound as a light yellow solid (0.48 g, 95%). Mass spectrum (MALDI-TOF, α-cyano-4-hydroxycinnamic acid matrix) calcd. for C$_{32}$H$_{41}$N$_5$O$_8$: 424.2 (M-2 Boc+H). Found: 425.3.

d) 9-Hydroxy-9-fluorenylcarbonyl-L-Pro-NH(CH$_2$)$_2$O—NH—C(=NH)NH$_2$trifluoroacetate

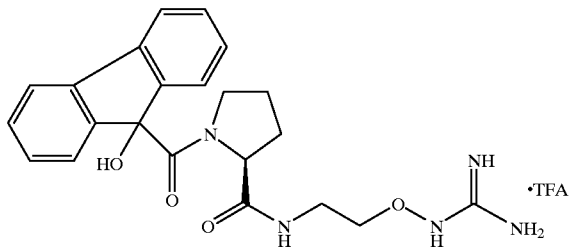

The title compound was prepared from the product of the preceding step (0.47 g, 0.75 mmol) in a manner analogous to Example 1, Procedure B, step i, as a white solid (0.32 g, 79%). $^1$H NMR (300 MHz, CDCl$_3$/CD$_3$OD) δ 7.68 (d, 2H, J=7 Hz), 7.59 (bs, 1H), 7.46–7.29 (m, 6H), 4.41 (dd, 1H, J=8 Hz, 5 Hz), 4.01 (qdd, 1H, J=14 Hz, 6 Hz, 3 Hz), 3.60 (ddd, 1H, J=15 Hz, 6 Hz, 3 Hz), 2.35 (qd, 2H, J=11 Hz, 7 Hz), 1.91 (dq, 1H, J=13 Hz, 7 Hz), 1.72 (sextet, 1H, J=6 Hz), 1.61 (sextet, 1H, J=7 Hz), 1.44 (sextet, 1H, J=6 Hz). Mass spectrum (MALDI-TOF, gentisic acid matrix) calcd. for C$_{22}$H$_{25}$N$_5$O$_4$: 446.2 (M+Na), 424.2 (M+H). Found: 446.1, 424.1.

EXAMPLE 4

9-Hydroxy-9-fluorenylcarbonyl-L-Pro-NH(CH$_2$)$_3$O—NH—C(=NH)NH$_2$trifluoroacetate

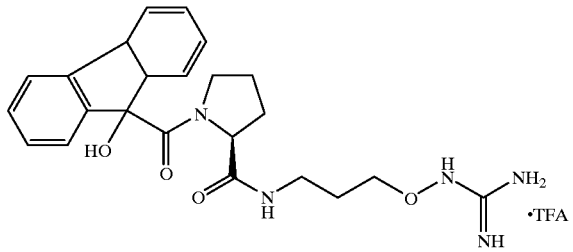

a) 3-(Benzyloxycarbonylamino)-1-propanol

To a solution of 3-amino-1-propanol (3.75 g, 50 mmol) in methylene chloride (40 mL) was slowly added benzyl chloroformate (3.40 g, 20 mmol) in methylene chloride (10 mL) at 0° C. and the mixture was stirred at 0° C. for 3 h. Additional methylene chloride (50 mL) was added, the solution washed with 10% citric acid (3×50 mL) and brine (50 mL), and dried over Na$_2$SO$_4$. After evaporating the solvent in vacuo, the residue was purified by filtration through silica gel (1:1 ethyl acetate:hexane) to give the title compound as a white solid (4.05 g, 97%). $^1$H-NMR (300 MHz, CDCl$_3$) δ 7.34 (m, 5H), 5.17 (bs, 11H), 5.10 (s, 2H), 3.66 (t, 2H, J=5.8 Hz), 3.33 (t, 2H, J=6.1 Hz), 2.63 (bs, 1H), 1.69 (pentet, 2H, J=6.1 Hz).

b) N-[3-(Benzyloxycarbonylamino)-1-propoxy]phthalimide

The title compound was prepared from the product of the preceding step (4.00 g, 19 mmol) in a manner analogous to Example 1, Procedure B, step a, as a white solid (6.85 g, 100%). $^1$H-NMR (300 MHz, CDCl$_3$) δ 7.83 (m, 2H), 7.77 (m, 2H), 7.36 (m, 5H), 5.67 (bs, 1H), 5.12 (s, 2H), 4.28 (t, 2H, J=5.8 Hz), 3.51 (q, 2H, J=6.1 Hz), 1.99 (pentet, 2H, J=6.0 Hz).

c) 3-(Benzyloxycarbonylamino)-1-propoxyamine

The title compound was prepared from the product of the preceding step (1.42 g, 4.0 mmol) in a manner analogous to Example 1, Procedure B, step b, as a white solid (0.87 g, 97%). $^1$H-NMR (300 MHz, CDCl$_3$) δ 7.36 (m, 5H), 5.38 (bs, 2H), 5.09 (s, 2H), 5.08 (bs, 1H), 3.73 (t, 2H, J=5.9 Hz), 3.29 (q, 2H, J=6.2 Hz), 1.79 (pentet, 2H, J=6.2 Hz).

d) [N,N'-Di(tert-butoxycarbonyl)]-3-(benzyloxycarbonylamino)-1-propoxyguanidine

The title compound was prepared from the product of the preceding step (0.86 g, 3.84 mmol) in a manner analogous to Example 1, Procedure B, step c, as a colorless oil (1.60 g, 89%). $^1$H-NMR (300 MHz, CDCl$_3$) δ 9.10 (bs, 1H), 7.74 (bs, 1H), 7.35 (m, 5H), 5.55 (bs, 1H), 5.10 (s, 2H), 4.12 (t, 2H, J=6.1 Hz), 3.32 (t, 2H, J=6.4 Hz), 1.87 (pentet, 2H, J=6.2 Hz), 1.50 (s, 9H), 1.47 (s, 9H).

e) [N,N'-Di(tert-butoxycarbonyl)]-3-amino-1-propoxyguanidine

The title compound was prepared from the product of the preceding step (0.76 g, 1.7 mmol) in a manner analogous to Example 1, Procedure B, step d, as a colorless oil (0.16 g, 28%). $^1$H-NMR (300 MHz, CDCl$_3$) δ 4.12 (t, 2H, J=6.1 Hz), 2.85 (t, 2H, J=6.7 Hz), 1.84 (pentet, 2H, J=6.2 Hz), 1.50 (s, 9H), 1.48 (s, 9H).

f) Fmoc-L-Pro-NH(CH$_2$)$_3$O—NH—C(=NBoc)NHBoc

The title compound was prepared from the product of the preceding step (0.40 g, 1.07 mmol) in a manner analogous to Example 3, step a, as a white solid (0.67 g, 99%). Mass spectrum (MALDI-TOF, α-cyano-4-hydroxycinnamic acid matrix) calcd. for C$_{34}$H$_{45}$N$_5$O$_8$: 452.2 (M-2 Boc+H). Found: 453.9.

g) L-Pro-NH(CH$_2$)$_3$O—NH—C(=NBoc)NHBoc

The title compound was prepared from the product of the preceding step (0.67 g, 1.02 mmol) in a manner analogous to Example 1, Procedure B, step f, as a white solid (0.23 g, 52%). Mass spectrum (MALDI-TOF, α-cyano-4-hydroxycinnamic acid matrix) calcd. for C$_{19}$H$_{35}$N$_5$O$_6$: 230.2 (M-2 Boc+H). Found: 230.7.

h) 9-Hydroxy-9-fluorenylcarbonyl-L-Pro-NH(CH$_2$)$_3$O—NH—C(=NBoc)NHBoc

The title compound was prepared from the product of the preceding step (0.22 g, 0.52 mmol) in a manner analogous to Example 3, step c, as a pale yellow solid (0.22 g, 67%). Mass spectrum (MALDI-TOF, α-cyano-4-hydroxycinnamic acid matrix) calcd. for C$_{33}$H$_{43}$N$_5$O$_8$: 438.2 (M-2 Boc+H). Found: 439.4.

i) 9-Hydroxy-9-fluorenylcarbonyl-L-Pro-NH(CH$_2$)$_3$O—NH—C(=NH)NH$_2$ trifluoroacetate The title compound was prepared from the product of the preceding step (0.22 g, 0.34 mmol) in a manner analogous to Example 1, Procedure B, step i, as a white solid (0.2 g, 100%). $^1$H NMR (300 MHz, CDCl$_3$/CD$_3$OD) δ 7.70 (d, 2H, J=7 Hz), 7.62 (m, 1H), 7.48–7.37 (m, 5H), 7.32 (m, 1H), 4.41 (dd, 1H, J=8 Hz, 5 Hz), 3.97 (m, 2H), 3.48 (m, 1H), 3.26 (m, 1H), 2.35 (t, 2H, J=7 Hz), 1.97–1.85 (m, 3H), 1.75 (sextet, 1H, J=6 Hz), 1.62 (sextet, 1H, J=7 Hz), 1.45 (sextet, 1H, J=6 Hz). Mass spectrum (MALDI-TOF, α-cyano-4-hydroxycinnamic acid matrix) calcd. for C$_{23}$H$_{27}$N$_5$O$_4$: 460.2 (M+Na), 438.2 (M+H). Found: 460.9, 438.8.

EXAMPLE 5

In vitro Inhibition of Purified Enzymes

Reagents: All buffer salts were obtained from Sigma Chemical Company (St. Louis, Mo.), and were of the highest purity available. The enzyme substrates, N-benzoyl-Phe-Val-Arg-p-nitroanilide (Sigma B7632), N-benzoyl-Ile-Glu-Gly-Arg-p-nitroanilide hydrochloride (Sigma B2291), N-p-Tosyl-Gly-Pro-Lys-p-nitroanilide (Sigma T6140), N-succinyl-Ala-Ala-Pro-Phe-p-nitroanilide (Sigma S7388) and N-CBZ-Val-Gly-Arg-p-nitroanilide (Sigma C7271) were obtained from Sigma. N-succinyl-Ala-Ala-Pro-Arg-p-nitroanilide (BACHEM L-1720) and N-succinyl-Ala-Ala-Pro-Val-p-nitroanilide (BACHEM L-1770) were obtained from BACHEM (King of Prussia, Pa.).

Human α-thrombin, human factor Xa and human plasmin were obtained from Enzyme Research Laboratories (South Bend, Ind.). Bovine α-chymotrypsin (Sigma C4129), bovine trypsin (Sigma T8642) and human kidney cell urokinase (Sigma U5004) were obtained from Sigma. Human leukocyte elastase was obtained from Elastin Products (Pacific, Mo.).

$K_i$ Determinations: All assays are based on the ability of the test compound to inhibit the enzyme catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for $K_m$. Test compounds are prepared as a 1.0 mg/ml solution in DMSO. Dilutions are prepared in DMSO yielding 8 final concentrations encompassing a 200 fold concentration range. Enzyme solutions are prepared at the concentrations listed below in assay buffer.

In a typical $K_i$ determination, into each well of a 96 well plate is pipetted 280 μL of substrate solution, 10 μL of test compound solution, and the plate allowed to thermally equilibrate at 37° C. in a Molecular Devices plate reader for >15 minutes. Reactions were initiated by the addition of a 10 μL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined $K_i$ value.

Thrombin: Thrombin activity was assessed as the ability to hydrolyze the substrate N-succinyl-Ala-Ala-Pro-Arg-p-nitroanilide. Substrate solutions were prepared at a concentration of 32 μM (32 μM<<Km=180 μM) in assay buffer. Final DMSO concentration was 4.3%. Purified human cc-thrombin was diluted into assay buffer to a concentration of 15 nM. Final reagent concentrations were: [thrombin]= 0.5 nM, [substrate N-succinyl-Ala-Ala-Pro-Arg-p-nitroanilide]=32 μM.

Factor X [FXa]: FXa activity was assessed as the ability to hydrolyze the substrate N-benzoyl-Ile-Glu-Gly-Arg-p-nitroanilide hydrochloride. Substrate solutions were prepared at a concentration of 51 μM (51<<$K_m$=1.3 mM) in assay buffer. Final DMSO concentration was 4.3%. Purified activated human Factor X was diluted into assay buffer to a concentration of 300 nM. Final reagent concentrations were: [FXa]=10 nM, [N-benzoyl-Ile-Glu-Gly-Arg-p-nitroanilide hydrochloride]=51 μM.

Plasmin: Plasmin activity was assessed as the ability to hydrolyze the N-p-Tosyl-Gly-Pro-Lys-p-nitroanilide. Substrate solutions were prepared at a concentration of 37 μM (37 μM<<$K_m$=243 μM) in assay buffer. Final DMSO concentration was 4.3%. Purified human plasmin was diluted into assay buffer to a concentration of 240 nM. Final reagent concentrations were: [Plasmin]=8 nM, [N-p-Tosyl-Gly-Pro-Lys-p-nitroanilide]=37 μM.

Chymotrypsin: Chymotrypsin activity was assessed as the ability to hydrolyze N-succinyl-Ala-Ala-Pro-Phe-p-nitroanilide. Substrate solutions were prepared at a concentration of 14 μM (14 μM<<$K_m$=62 μM) in assay buffer. Final DMSO concentration was 4.3%. Purified bovine chymotrypsin was diluted into assay buffer to a concentration of 81 nM. Final reagent concentrations were: [Chymotrypsin]=2.7 nM, [N-succinyl-Ala-Ala-Pro-Phe-p-nitroanilide]=14 μM.

Trypsin: Trypsin activity was assessed as the ability to hydrolyze N-benzoyl-Phe-Val-Arg-p-nitroanilide. Substrate solutions were prepared at a concentration of 13 μM (13 μM<<$K_m$=291 μM) in assay buffer. Final DMSO concentration was 4.3%. Purified bovine trypsin was diluted into assay buffer to a concentration of 120 nM. Final reagent concentrations were: [Trypsin]=4 nM, [N-benzoyl-Phe-Val-Arg-p-nitroanilide]=13 μM.

Elastase: Elastase activity was assessed as the ability to hydrolyze N-succinyl-Ala-Ala-Pro-Val-p-nitroanilide. Substrate solutions were prepared at a concentration of 19 μM (19 μM<<$K_m$=89 μM) in assay buffer. Final DMSO concentration was 4.3%. Purified human leukocyte elastase was diluted into assay buffer to a concentration of 750 nM. Final reagent concentrations were: [Elastase]=25 nM, [N-succinyl-Ala-Ala-Pro-Val-p-nitroanilide]=19 μM.

Urokinase: Urokinase activity was assessed as the ability to hydrolyze N-CBZ-Val-Gly-Arg-p-nitroanilide. Substrate solutions were prepared at a concentration of 100 μM (100 μM<$K_m$=1.2 mM) in assay buffer. Final DMSO concentration was 4.3%. Purified human kidney urokinase was diluted into assay buffer to a concentration of 1.2 μM. Final reagent concentrations were: [Urokinase]=40 nM, and N-CBZ-Val-Gly-Arg-p-nitroanilide]=100 mM.

The compound of Example 1 had a $K_i$ for thrombin of 20 nM.

The results indicate that the compounds of the present invention are inhibitors of proteases, including thrombin.

EXAMPLE 6

Tablets for Oral Administration 1000 tablets are prepared from the following ingredients:

| | |
|---|---|
| Active compound | 100 g |
| Lactose | 200 g |
| Polyvinyl pyrrolidone | 30 g |
| Microcrystalline cellulose | 30 g |
| Magnesium stearate | 6 g |

The active constituent and lactose are mixed with an aqueous solution of polyvinyl pyrrolidone. The mixture is dried and milled to form granules. The microcrystalline cellulose and then the magnesium stearate are then admixed. The mixture is then compressed in a tablet machine giving 1000 tablets, each containing 100 mg of active constituent.

EXAMPLE 7

Solution for Parenteral Administration

A solution is prepared from the following ingredients:

| | |
|---|---|
| Active compound | 5 g |
| Sodium chloride for injection | 6 g |

| | |
|---|---|
| Sodium hydroxide for pH adjustment at pH | pH 5–7 |
| Water for inj. | Up to 1000 ml |

The active constituent and the sodium chloride are dissolved in the water. The pH is adjusted with 2M NaOH to pH 3–9 and the solution is filled into sterile ampoules.

EXAMPLE 8

Inhaler Powder

The active compound is micronized in a jet mill to a particle size suitable for inhalation (mass diameter<4 μm).

100 mg of the micronized powder is filled into a powder multidose inhaler (Turbohaler®). The inhaler is equipped with a dosing unit which delivers a dose of 1 mg.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

ABBREVIATIONS

Ac=acetyl
Aze=azetidine-2-carboxylic acid
betapic=piperidine-3-carboxylic acid
Boc=tert-butyloxycarbonyl
Bop=benzotriazole-1-yl-oxy-tris-(dimethylamino)-phosphonium hexafluoro-phosphate
Bn=benzyl
Bu=butyl
Cbz=benzyloxycarbonyl
Cgl=cyclohexylglycine
Cha=β-cyclohexyl alanine
Chx=cyclohexyl
CME-CDI=1-cyclohexyl-3-(2-morpholinoethyl) carbodiimide metho-p-toluenesulfonate
DBU=1,8-diazabicyclo[5.4.0]undec-7-ene
Dca=dicyclohexylalanine
DCC=dicyclohexyl carbodiimide
DCU=dicyclohexyl urea
DMAP=N,N-dimethyl amino pyridine
DMF=dimethyl formamide
DMSO=dimethyl sulphoxide
Dpa=diphenylalanine
EDC=1-(3-dimethylaminopropyl)-3-ethylcarbodiimide hydrochloride
Et=ethyl
Etoac=ethyl acetate
EtOh=ethanol
Gly=glycine
h=hours
HATU=O-(7-azabenzotriazole-1-yl)-1,1,3,3-tetramethyluronium hexafluoro-phosphate
HCl=hydrochloric acid
Hex=hexyl
HOAc=acetic acid
HOBt=N-hydroxy benzotriazole
HOC=Homocyclohexyl alanine
Hop=Homophenyl alanine
Me=methyl
MeOH=methanol
Ms=mesyl
NGn=—NH—NH—C(=NH)—NH$_2$
NMM=N-methyl morpholine
OGn=—O—NH—C(=NH)—NH$_2$
Pd/C=palladium on charcoal
Pgl=phenyl glycine
Ph=phenyl
Phe=phenyl alanine
Pic=pipecolinic acid
Pro=proline
RPLC=Reverse phase high performance liquid chromatography
Tf=trifluoromethylsulfonyl
TFA=trifluoroacetic acid
THF=tetrahydrofuran
Tic=1-carboxy-1,2,3,4-tetrahydroisoquinoline
Ts=tosyl
Val=valine
Z=benzyloxy carbonyl

What is claimed is:

1. A compound having the Formula I, including stereoisomers:

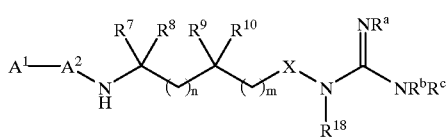

I or a solvate, hydrate or pharmaceutically acceptable salt thereof; wherein:

$A^1$ represents a structural fragment of Formula IIa, IIb, IIc, IId, IIe, IIf or IIg:

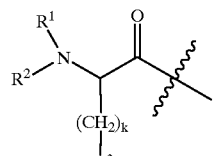

IIa

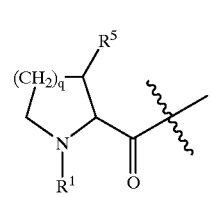

IIb

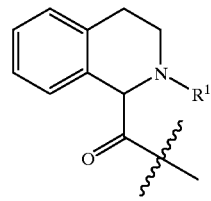

IIc

-continued

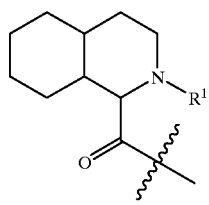

IId

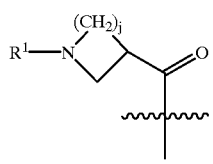

IIe

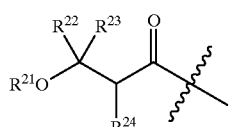

IIf

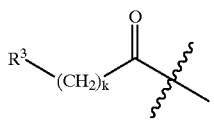

IIg wherein:

k is an integer 0, 1, 2, 3 or 4;
j is an integer 1, 2, 3 or 4;
q is an integer 0, 1, 2 or 3;

$R^1$ represents H, $C_{1-4}$ alkyl, or $R^{11}OOC$—$(C_{1-4})$alkyl-, optionally substituted in the position which is alpha to the carbonyl group, with a group $R^{14}$—$(CH_2)_p$—, wherein p is 0, 1 or 2 and $R^{14}$ is methyl, phenyl, OH, $COOR^{12}$, $CONHR^{12}$, where $R^{12}$ is H or $C_{1-4}$ alkyl group, and $R^{11}$ is H, $C_{1-6}$ alkyl, or benzyl substituted in the 4-position by $COOR^{12}$, where $R^{12}$ is as defined above, or $R^1$ represents $R^{13}$—NH—CO—$(C_{1-4})$alkyl-, optionally substituted alpha to the carbonyl with $C_{1-4}$ alkyl and where $R^{13}$ is H, $C_{1-4}$ alkyl or —$CH_2COOR^{12}$, where $R^{12}$ is as defined above, or $R^1$ represents $R^{12}OOC$—$CH_2$—OOC-alkyl-, where the alkyl group has 1 to 4 carbon atoms and is optionally substituted alpha to the carbonyl with $C_{1-4}$ alkyl and where $R^{12}$ is as defined above, or $R^1$ represents $C_{1-4}$ alkylsulfonyl, Ph(4-$COOR^{12}$)—$SO_2$—, Ph(3-$COOR^{12}$)—$SO_2$—, Ph(2-$COOR^{12}$)—$SO_2$—, where $R^{12}$ is as defined above, or $R^1$ represents $C_{1-4}$ alkylcarbonyl, or $R^1$ represents $C_{1-4}$ alkoxycarbonyl, or $R^1$ represents —CO—$(CH_2)_p$—$COOR^{12}$, where $R^{12}$ is as defined above and p is an integer 0, 1 or 2, or $R^1$ represents —$CH_2PO(OR^{15})_2$, —$CH_2SO_3H$ or —$CH_2$—(5-(1H)-tetrazolyl), where $R^{15}$ is, individually at each occurrence, H, methyl or ethyl;

$R^2$ represents H or $C_{1-4}$ alkyl, carboxy($C_{1-4}$)alkyl or $C_{1-4}$ alkoxycarbonyl($C_{1-4}$)alkyl;

$R^3$ represents $C_{1-4}$ alkyl, optionally having one or more fluorine atoms, or $R^3$ represents cyclopentyl, cyclohexyl or phenyl, any of which may be optionally substituted with $C_{1-4}$ alkyl, or $R^3$ represents fluoren-9-yl, or 9-hydroxyfluoren-9-yl, or $R^3$ represents a phenyl group substituted with one to three $OR^{16}$, where $R^{16}$ is independently H or $C_{1-4}$ alkyl and k is 0, 1, or $R^3$ represents a 1-naphthyl or 2-naphthyl group and k is 0, 1, or $R^3$ represents a cis- or trans-decalin group and k is 0, 1, or $R^3$ represents 4-pyridyl, 3-pyrrolidyl or 3-indolyl, any of which is optionally substituted with $OR^{16}$, where $R^{16}$ is as defined above and k is 0, 1, or $R^3$ represents $Si(Me)_3$ or $CH(R^{17})_2$, wherein $R^{17}$ is independently $C_{1-4}$ alkyl, cyclopentyl, cyclohexyl, benzyl or phenyl, or, in Formula IIa, where one $R^{17}$ is cyclopentyl, cyclohexyl or phenyl, and the other $R^{17}$ forms an ethylene bridge together with $R^1$ and k is 0, 1, or 2;

$R^5$ represents $C_{1-4}$ alkyl, phenyl, or benzyl;

$R^{21}$ represents H, $C(O)R^{41}$, $SiR^{42}R^{43}R^{44}$ or $C_{1-6}$ alkyl which latter group is optionally substituted or terminated by one or more substituents selected from $OR^{45}$ or $(CH_2)_tR^{46}$;

$R^{42}$, $R^{43}$ and $R^{44}$ independently represent H, phenyl or $C_{1-6}$ alkyl;

$R^{46}$ represents $C_{1-4}$ alkyl, phenyl, OH, $C(O)OR^{47}$ or $C(O)N(H)R^{48}$;

$R^8$ represents H, $C_{1-4}$ alkyl or $CH_2C(O)OR^{49}$;

$R^{45}$ and $R^{47}$ independently represent H, $C_{1-4}$ alkyl or $C_{7-9}$ alkylphenyl;

$R^{41}$ and $R^{49}$ independently represent H or $C_{1-4}$ alkyl; and t represents 0, 1 or 2;

$R^{22}$ and $R^{23}$ independently represent H, $C_{1-4}$ alkyl, cyclohexyl or phenyl;

$R^{24}$ represents a structural fragment of Formula IVa, IVb or IVc,

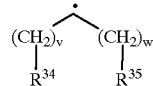

IVa

IVb

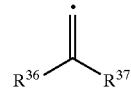

IVc wherein v, w and u independently represent 0, 1, 2, 3 or 4;

$R^{34}$ and $R^{35}$ independently represent H, $Si(Me)_3$, 1- or 2-naphthyl, a polycyclic hydrocarbyl group, $CHR^{31}R^{32}$ or $C_{1-4}$ alkyl (which latter group is optionally substituted by one or more fluorine atoms), or $C_{3-8}$ cycloalkyl, phenyl, methylenedioxyphenyl, benzodioxanyl, benzofuranyl, dihydrobenzofuranyl, benzothiazolyl, benzoxazolyl, benzimidazolyl, coumaranonyl, coumarinyl or dihydrocoumarinyl (which latter twelve groups are optionally substituted by one or more of $C_{1-4}$ alkyl (which latter group is optionally substituted by one or more halo substituent), $C_{1-4}$ alkoxy, halo, hydroxy, cyano, nitro, $SO_2NH_2$, $C(O)OH$ or $N(H)R^{33}$);

$R^{31}$ and $R^{32}$ independently represent cyclohexyl or phenyl;

$R^{36}$ and $R^{37}$ independently represent H, $C_{1-4}$ alkyl, $C_{3-8}$ cycloalkyl, phenyl (which latter group is optionally substituted by one or more of $C_{1-4}$ alkyl (which latter group is optionally substituted by one or more halo substituent), $C_{1-4}$ alkoxy, halo, hydroxy, cyano, nitro, $SO_2NH_2$, C(O)OH or N(H)$R^{38}$) or together with the carbon atom to which they are attached form a $C_{3-8}$ cycloalkyl ring;

$R^{33}$ and $R^{38}$ independently represent H or C(O)$R^{39}$;

and $R^{39}$ represents H, $C_{1-4}$ alkyl or $C_{1-4}$ alkoxy;

$A^2$ represents a structural fragment of Formula IIIa, IIIb or IIIc:

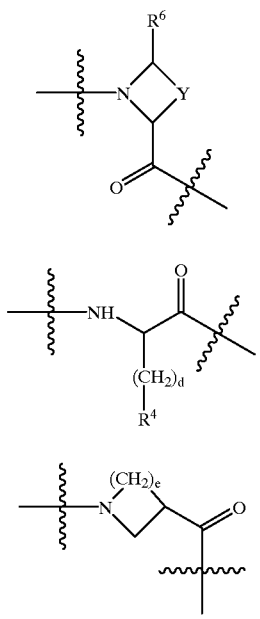

IIIa

IIIb

IIIc wherein:

d is 0, 1 or 2;

e is 1, 2, 3 or 4;

Y represents a methylene group, or

Y represents an ethylene group and the resulting 5-membered ring may optionally carry one or two fluorine atoms, a hydroxy group or an oxo group in position 4, or may or may not be unsaturated, or Y represents —$CH_2$—O—, —$CH_2$—S—, —$CH_2$—SO—, with the heteroatom functionality in position 4, or Y represents a n-propylene group and the resulting 6-membered ring may optionally carry in position 5 one fluorine atom, a hydroxy group or an oxo group, carry two fluorine atoms in one of positions 4 or 5 or be unsaturated in position 4 and 5, or carry in position 4 a $C_{1-4}$ alkyl group, or Y represents —$CH_2$—$CH_2$—, $CH_2$—S—$CH_2$—, —$CH_2$—SO—$CH_2$—, or Y represents —$CH_2H_2$—$CH_2$—$CH_2$—;

$R^3$ is as defined as for $R^4$ above;

$R^6$ represents H or $C_{1-4}$ alkyl, carboxy, $C_{1-4}$ alkoxycarbonyl, carboxy($C_{1-4}$)alkyl or $C_{1-4}$ alkoxycarbonyl($C_{1-4}$)alkyl;

provided that when $A^1$ is a fragment of Formula IIb, and $A^2$ is a fragment of Formula IIIb, then $R^4$ is not 1-naphthyl or 2-naphthyl;

$R^7$ is one of hydrogen, alkyl, aralkyl, aryl, hydroxyalkyl, aminoalkyl, monoalkylaminoalkyl, dialkylaminoalkyl, carboxyalkyl, hydroxy, alkoxy, aralkoxy, aryloxy, heteroaryloxy, or mono- or di-alkylamino, provided that n is other than zero when $R^7$ is hydroxy, alkoxy, aralkoxy, aryloxy, heteroaryloxy, or mono- or di-alkylamino;

$R^8$, $R^9$ and $R^{10}$ are each independently one of hydrogen, alkyl, aralkyl, aryl, hydroxyalkyl, aminoalkyl, monoalkylaminoalkyl, dialkylaminoalkyl or carboxyalkyl;

or $R^7$ and $R^8$ are taken together to form —$(CH_2)_i$—, where i is zero (a bond), 1 or 2, while $R^9$ and $R^{10}$ are defined as above; or $R^7$ and $R^{10}$ are taken together to form —$(CH_2)_j$—, where j is zero (a bond), or 1 to 8, while $R^8$ and $R^9$ are defined as above; or $R^9$ and $R^{10}$ are taken together to form —$(CH_2)_h$—, where h is 2–8, while $R^7$ and $R^8$ are defined as above;

$R^{18}$ is one of hydrogen, alkyl, alkenyl, alkynyl, aralkyl, aryl, hydroxyalkyl, aminoalkyl, monoalkylamino($C_{2-10}$)alkyl, dialkylamino($C_{2-10}$)alkyl or carboxyalkyl, or alternatively, $R^{18}$ and $R^{10}$ taken together to form —$(CH_2)_w$—, where w is 1–5;

X is oxygen;

$R^a$, $R^b$ and $R^c$ are independently hydrogen, alkyl, hydroxy, alkoxy, aryloxy, aralkoxy, alkoxycarbonyloxy, cyano or —$CO_2R^w$;

$R^w$ is alkyl, cycloalkyl, phenyl, benzyl,

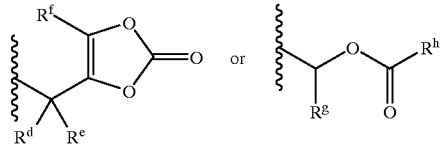

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n is from zero to 8; and m is from zero to 4.

2. A compound of claim 1, wherein $R^7$, $R^8$, $R^9$ and $R^{10}$ are independently one of hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl.

3. A compound of claim 2, wherein $R^7$, $R^8$, $R^9$ and $R^{10}$ are hydrogen.

4. A compound of claim 1, wherein $R^7$ and $R^8$ are taken together to form —$(CH_2)_i$— and where i is 2, 3 or 4.

5. A compound of claim 1, wherein $R^9$ and $R^{10}$ are taken together to form —$(CH_2)_h$— and where h is 2.

6. A compound of claim 1, wherein $R^{18}$ represents H, $C_{1-4}$ alkyl, carboxy, $C_{1-4}$ alkoxycarbonyl, carboxy($C_{1-4}$)alkyl, $C_{1-4}$ alkoxycarbonyl($C_{1-4}$)alkyl, ($C_{6-10}$)ar($C_{1-6}$)alkyl, or $C_{3-6}$ alkenyl.

7. A compound of claim 6, wherein $R^{18}$ is hydrogen or $C_{1-6}$ alkyl.

8. A compound of claim 1, wherein $R^{18}$ and $R^{10}$ are taken together to form —$(CH_2)_w$—, where w is 1–5.

9. A compound of claim 1, wherein $R^a$, $R^b$ and $R^c$ are independently hydrogen, hydroxy, $C_{1-6}$ alkyl, $C_{1-6}$ alkoxy, cyano or —$CO_2R^w$, where $R^w$, in each instance, is $C_{1-4}$ alkyl, $C_{4-7}$ cycloalkyl or benzyloxycarbonyl.

10. A compound of claim 1, wherein $R^b$ and $R^c$ are each hydrogen.

11. A compound of claim 1, wherein $R^a$, $R^b$ and $R^c$ independently represent the group —$CO_2R^w$, where $R^w$ is one of

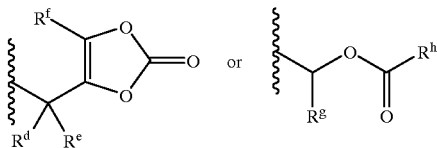

and where $R^d$–$R^h$ are defined as in claim 1.

12. A compound of claim 11, wherein $R^d$, $R^e$ and $R^g$ are hydrogen, $R^f$ is methyl, and $R^h$ is benzyl or tert-butyl.

13. A compound of claim 1, wherein n is from zero to 4, and m is from zero to 4.

14. A compound of claim 1, wherein n is zero, 1 or 2, and m is zero, 1, 2 or 3.

15. A compound of claim 1, wherein $A^1$ represents a structural fragment of Formula IIa, IIb, IIc, IId, or IIg, wherein:

k is an integer 0, 1, 2, 3 or 4;

q is an integer 0, 1, 2 or 3;

$R^1$ represents H, $C_{1-4}$ alkyl, $R^{11}OOC$—$(C_{1-4})$alkyl-, optionally substituted in the position which is alpha to the carbonyl group, and the alpha substituent is a group $R^{14}$—$(CH_2)_p$—, wherein p is 0, 1 or 2 and $R^{14}$ is methyl, phenyl, OH, $COOR^{12}$, $CONHR^{12}$, where $R^{12}$ is H or $C_{1-4}$ alkyl, and $R^{11}$ is H or $C_{1-6}$ alkyl, or $R^1$ represents Ph(4-$COOR^{12}$)—$CH_2$—, where $R^{12}$ is as defined above, or $R^1$ represents $R^{13}$—NH—CO—$(C_{1-4})$alkyl-, and is optionally substituted alpha to the carbonyl with $C_{1-4}$ alkyl, and where $R^{13}$ is H or $C_{1-4}$ alkyl or —$CH_2COOR^{12}$ where $R^{12}$ is as defined above, or $R^1$ represents $R^{12}OOC$—$CH_2$—OOC—$(C_{1-4})$alkyl-, where the alkyl is optionally substituted alpha to the carbonyl with $C_{1-4}$ alkyl and where $R^{12}$ is as defined above, or $R^1$ represents $C_{1-4}$ alkylsulfonyl, Ph(4-$COOR^{12}$)—$SO_2$—, Ph(3-$COOR^{12}$)—$SO_2$—, Ph(2-$COOR^{12}$)—$SO_2$— where $R^{12}$ is as defined above or $R^1$ represents $C_{1-4}$ alkylcarbonyl, or $R^1$ represents $C_{1-4}$ alkoxycarbonyl, or $R^1$ represents —CO—$(CH_2)_p$—$COOR^{12}$, where $R^{12}$ is as defined above and p is an integer 0, 1 or 2, or $R^1$ represents —$CH_2PO(OR^{15})_2$, —$CH_2SO_3H$ or —$CH_2$-(5-(1H)-tetrazolyl), where $R^{15}$ is, individually at each occurrence, H, methyl or ethyl;

$R^2$ represents H or $C_{1-4}$ alkyl, carboxy($C_{1-4}$)alkyl or $C_{1-4}$ alkoxycarbonyl($C_{1-4}$)alkyl;

$R^3$ represents $C_{1-4}$ alkyl, optionally substituted by one or more fluorine atoms, or $R^3$ represents cyclopentyl, cyclohexyl or phenyl, any of which may be optionally substituted with $C_{1-4}$ alkyl, or $R^3$ represents a 1-naphthyl or 2-naphthyl group and k is 0, 1, or $R^3$ represents a cis- or trans-decalin group and k is 0, 1, or $R^3$ represents $Si(Me)_3$ or $CH(R^{17})_2$, wherein $R^{17}$ is independently propyl, cyclopentyl, cyclohexyl, benzyl, or phenyl, or $R^3$ represents fluoren-9-yl or 9-hydroxy-fluoren-9-yl;

$A^2$ represents a structural fragment of Formula IIIa, IIIb or IIIc, wherein:

d is an interger 0, 1 or 2;

e is an integer 1, 2, 3 or 4;

Y represents a methylene group, or

Y represents an ethylene group and the resulting 5-membered ring may optionally carry one or two fluorine atoms, a hydroxy group or an oxo group in position 4, or may optionally be unsaturated, or Y represents —$CH_2$—O—, —$CH_2$—S—, —$CH_2$—SO—, with the heteroatom functionality in position 4, or Y represents a n-propylene group and the resulting 6-membered ring may optionally carry in position 5 one fluorine atom, a hydroxy group or an oxo group, carry two fluorine atoms in one of positions 4 or 5 or be unsaturated in position 4 and 5, or carry in position 4 a $C_{1-4}$ alkyl group, or Y represents —$CH_2$—O—$CH_2$—, —$CH_2$—S—$CH_2$—, —$CH_2$—SO—$CH_2$—, or Y represents —$CH_2$—$CH_2$—$CH_2$—$CH_2$;

$R^4$ represents $C_{1-4}$ alkyl, or $R^4$ represents a $Si(Me)_3$ group;

$R^6$ represents H or $C_{1-4}$ alkyl, or $R^6$ represents —$(CH_2)_p$—$COOR^{51}$, where p is 0, 1 or 2 and $R^{51}$ is H or $C_{1-4}$ alkyl;

$R^a$, $R^b$ and $R^c$ are each one of hydrogen, $C_{1-4}$ alkyl, hydroxy, $C_{1-4}$ alkoxy, phenoxy, $C_{1-4}$ alkyloxycarbonyl, benzyloxycarbonyl, cyano,

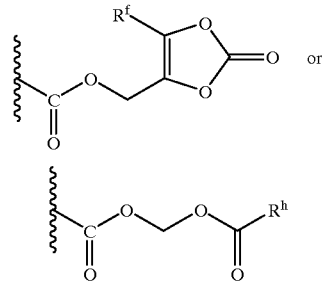

where $R^h$ is benzyl, methyl, ethyl, isopropyl, sec-butyl or t-butyl, and where $R^f$ is hydrogen or $C_{1-6}$ alkyl;

$R^7$, $R^8$, $R^9$ and $R^{10}$ are independently one of hydrogen, $C_{1-6}$ alkyl, $C_{2-10}$ carboxyalkyl or $C_{2-10}$ hydroxyalkyl, or $R^7$ and $R^8$ are taken together to form —$(CH_2)_i$— where i is zero, 1 or 2, while $R^9$ and $R^{10}$ are defined as above; or $R^7$ and $R^{10}$ are taken together to form —$(CH_2)_j$—, where j is zero (a bond), or 1, 2 or 3, while $R^8$ and $R^9$ are defined as above; or $R^9$ and $R^{10}$ are taken together to form —$(CH_2)_h$—, where h is 2, 3, or 4, while $R^7$ and $R^8$ are defined as above;

$R^{18}$ is one of hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, mono($C_{1-4}$)alkylamino($C_{2-8}$)alkyl, di($C_{1-4}$)alkylamino($C_{2-8}$)alkyl or $C_{2-10}$ carboxyalkyl, or alternatively, $R^{18}$ and $R^{18}$ taken together to form —$(CH_2)_w$—, where w is 1–5;

X is —O—;

n is from zero to 4; and m is from zero to 4.

16. A compound of claim 15, wherein $A^1$ represents IIa, IIb or IIg.

17. A compound of claim 16, wherein $A^2$ represents IIIa.

18. A compound of claim 17, wherein $R^1$ represents $R^{11}C$—$(C_{1-4})$alkyl-, and $R^{11}$ is H.

19. A compound of claim 18, wherein k is 0 or 1, and q is 1.

20. A compound of claim 15, wherein $R^6$ represents $(CH_2)_p$—$COOR^{51}$, where p is 0 and $R^{51}$ is H.

21. A compound of claim 1, wherein $A^1$ represents a structural fragment of Formula IIa, wherein:

k is 0 or 1;

$R^1$ represents $R^{11}OOC$—$(C_{1-4})$alkyl and $R^{11}$ is H;

$R^2$ represents H;

$R^3$ represents a cyclohexyl group;

$A^2$ represents a structural fragment of Formula IIIa, wherein:

Y represents a methylene group, an ethylene group, or a n-propylene group and the resulting 6-membered ring may optionally carry in position 4 a $C_{1-4}$ alkyl group;

$R^6$ represents H;

$R^a$, $R^b$ and $R^c$ are hydrogen, hydroxy,

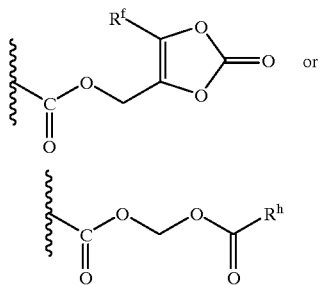

or where $R^h$ is benzyl or t-butyl, and where $R^f$ is hydrogen or methyl;

$R^7$, $R^8$, $R^9$ and $R^{10}$ are independently one of hydrogen, $C_{1-6}$ alkyl, $C_{2-10}$ hydroxyalkyl or $C_{2-10}$ carboxyalkyl, or $R^7$ and $R^8$ are taken together to form —$(CH_2)_i$— where i is zero, 1 or 2, while $R^9$ and $R^{10}$ are defined as above; or $R^7$ and $R^{10}$ are taken together to form —$(CH_2)_j$—, where j is zero (a bond), or 1, 2 or 3, while $R^8$ and $R^9$ are defined as above; or $R^9$ and $R^{10}$ are taken together to form —$(CH_2)_h$, where h is 2, 3 or 4, while $R^7$ and $R^8$ are defined as above;

$R^{18}$ is hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$)alkyl, or methylamino($C_{2-8}$)alkyl;

X is —O—;

$R^{19}$ is hydrogen, or $C_{1-6}$ alkyl;

n is from zero to 4; and m is zero, 1, 2 or 3.

22. A compound of claim 23, wherein $R^1$ represents $R^{11}OOC(C_{1-2})$alkyl and $R^{11}$ is H.

23. A compound of claim 21, wherein Y represents methylene or ethylene.

24. A compound of claim 1, wherein $A^1$ represents a structural fragment of Formula IIf;

$R^{21}$ represents optionally substituted $C_{1-6}$ alkyl or H;

$R^{24}$ represents a structural fragment of Formula IVa;

$A^2$ represents a structural fragment of Formula IIIa;

Y represents $CH_2$ or $(CH_2)_2$; and n represents 1.

25. A compound of claim 1, wherein $A^1$ represents a structural fragment of Formula IIg;

k is zero or 1;

$R^3$ represents phenyl or benzyl, optionally substituted by one to three of $OR^{16}$, where $R^{16}$ is hydrogen or methyl, or $R^3$ represents fluoren-9-yl or 9-hydroxyfluoren-9-yl, or $R^3$ represents $CH(R^{17})_2$, where $R^{17}$ is cyclohexyl or phenyl;

$A^2$ represents a structural fragment of Formula IIIa;

Y represents $CH_2$ or $(CH_2)_2$; and n represents 1.

26. A compound of claim 1, wherein $A^2$ is a fragment

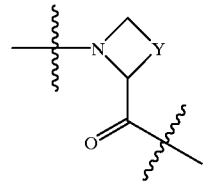

in the S-configuration.

27. A compound of claim 1, having the Formula Ia or Formula Ib:

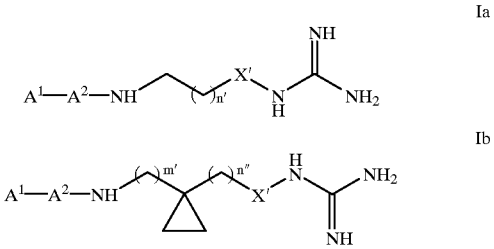

or a pharmaceutically acceptable salt or prodrug thereof; where:

n' is 1, 2 or 3;

n" is 0, 1, 2 or 3;

m' is 0, 1, 2 or 3;

X' is —O—; and combinations of $A^1$ and $A^2$ result in the following $A^1$—$A^2$— fragments:

HOOC—$CH_2$—(R)Cgl-Aze—
HOOC—$CH_2$—$CH_2$—(R)Cgl-Aze—
HOOC—$CH_2$—(R)Cgl-Pro—
HOOC—$CH_2$—$CH_2$—(R)Cgl-Pro—
(HOOC—$CH_2$)$_2$—(R)Cgl-Pro—
H—(R)Cgl-Pic—
HOOC—$CH_2$—(R,S)CH(COOH)—(R)Cgl-Pic—
H—(R)Cha-Aze—
HOOC—$CH_2$—(R)Cha-Aze—
HOOC—$CH_2$—(RorS)CH(COOH)—(R)Cha-Aze—
HOOC—$CH_2$—$CH_2$—(R)Cha-Aze—
HOOC—$CH_2$—NH—CO—$CH_2$—(R)Cha-Aze—
H—(R)Cha-Pro-Pab
HOOC—$CH_2$—(R)Cha-Pro—
HOOC—$CH_2$-(Me)(R)Cha-Pro—
HOOC—$CH_2$—$CH_2$—(R)Cha-Pro—
HOOC—$CH_2$—$CH_2$-(Me)(R)Cha-Pro—
HOOC—$CH_2$—(RorS)CH(COOH)—(R)Cha-Pro—
HOOC—$CH_2$—NH—CO—$CH_2$—(R)Cha-Pro—
EtOOC—$CH_2$—$CH_2$—$CH_2$—(R)Cha-Pro—
Ph(4-COOH)—$SO_2$—(R)Cha-Pro—
H—(R)Cha-Pic—
HOOC—$CH_2$—(R)Cha-Pic—
HOOC—$CH_2$—(RorS)CH(COOH)—(R)Cha-Pic—
HOOC—$CH_2$—$CH_2$—(R)Cha-Pic—
HOOC—CO—(R)Cha-Pic—
HOOC—$CH_2$—CO—(R)Cha-Pic—

Me-OOC—CH₂—CO—(R)Cha-Pic—
H₂N—CO—CH₂—(R)Cha-Pic—
Boc—(R)Cha-Pic—
Ac—(R)Cha-Pic—
Me-SO₂—(R)Cha-Pic—
H—(R)Cha-(R,S)betaPic—
HOOC—CH₂—CH₂—(R)Cha-(R,S)betaPic—
HOOC—CH₂—(R)Cha-Val—
HOOC—CH₂—CH₂—(R)Cha-Val—
H—(R)Hoc-Aze—
HOOC—CH₂—CH₂—(R)Hoc-Aze—
HOOC—CH₂—(R,S)CH(COOH)—(R)Hoc-Pro—
HOOC—CH₂—(R)Hoc-Pic—
(HOOC—CH₂)₂—(R)Hoc-Pic—
HOOC—CH₂—(R)Pro(3-(S)Ph)-Pro—
HOOC—CH₂—CH₂—(R)Pro(3-(S)Ph)-Pro—
HOOC—CH₂—CH₂—(R)Tic-Pro—
HOOC—CH₂—CH₂—(R)Cgl-Aze—
HOOC—CH₂—CH₂—(R)Cgl-Pro—
H—(R)Cha-Aze—
HOOC—CH₂—(R)Cgl-Aze—
H—(R)Cha-Pro—
H—(R)Cgl-Ile—
H—(R)Cgl-Aze—
HOOC—(R,S)CH(Me)-(R)Cha-Pro—
MeOOC—CH₂—(R)Cgl-Aze—
EtOOC—CH₂—(R)Cgl-Aze—
ⁿBuOOC—CH₂—(R)Cgl-Aze—
ⁿHexOOC—CH₂—(R)Cgl-Aze—
H—(R)Cgl-Pro—
HOOC—CH₂—(R)Cha-Pro—
HOOC—CH₂—CH₂—(R)Cgl-Pro—
HOOC—CH₂—CH₂—(R)Cha-Aze—
HOOC—CH₂—(R)Cha-Aze—
HOOC—CH₂—(R)Cha-Pro—
HOOC—CH₂—CH₂—(R)Cha-Pro—
(HOOC—CH₂)₂—(R)Cgl-Pro—
HOOC—CH₂CH₂(HOOC—CH₂)R)Cha-Pro—
H—(R)Phe-Cha—
HOOC—CH₂—(R)Phe-Cha—
H—(R)Cha-Cha—
HOOC—CH₂—(R)Cha-Cha—
H—(R)Cha-Pro—
Me-(R)Cha-Pro—
HO—(CH₂)₃—(R)Cha-Pro—
HOOC—CH₂—(R)Cha-Pro—
ⁱPrOOC—CH₂—(R)Cha-Pro—
HOOC—CH₂-(Me)(R)Cha-Pro—
HOOC—(R,S)CH(Me)-(R)Cha-Pro—
HOOC—(R,S)CH(CH₂CH₂Ph)-(R)Cha-Pro—
HOOC—CH₂—CH₂—(R)Cha-Pro—
EtOOC—CO—(R)Cha-Pro—
(R,S)Bla-(R)Cha-Pro—
HOOC—CH₂—(nBu)(R)Cha-Pro—
HOOC—(R,S)CH(Me)-(R)Cha-Pro—
EtOOC—(R,S)CH(Me)-(R)Cha-Pro—
HOOC—(R)CH(CH₂—OH)—(R)Cha-Pro—
HOOC—(R,S)CH(Ph)-(R)Cha-Pro—
HOOC—(S)CH(CH₂CH₂Ph)-(R)Cha-Pro—
HOOC—(R)CH(CH₂CH₂Ph)-(R)Cha-Pro—
HOOC—CO—(R)Cha-Pro—
MeOOC—CO—(R)Cha-Pro—
HOOC—(R,S)CH(CH₂COOH)—(R)Cha-Pro—
MeOOC—(R,S)CH(CH₂COOMe)-(R)Cha-Pro—
HOOC-Ph4-CH₂—(R)Cha-Pro—
(HO)₂P(O)—CH₂—(R)Cha-Pro—
EtO(HO)P(O)—CH₂—(R)Cha-Pro—
(EtO)₂P(O)H₂.

28. A compound of claim 27, having Formula Ia, wherein n' is 1 or 2.

29. A compound of claim 27, having Formula Ib, or a pharmaceutically acceptable salt or prodrug thereof, where X' is —O—.

30. A compound of claim 27, having Formula Ib, wherein n" is 0 or and m' is 0 or 1.

31. A compound of claim 27, having Formula Ia, wherein combinations of A¹ and A² result in an A¹—A²— fragment selected from the group consisting of HOOC—CH₂-(Me) (R)Cha-Pro— and HOOC—CH₂—(R)Cha-Pic—.

32. A compound of claim 27, having Formula Ib, wherein combinations of A¹ and A² result in an A¹—A²— fragment selected from the group consisting of HOOC—CH₂-(Me) (R)Cha-Pro— and HOOC—CH₂—(R)Cha-Pic—.

33. A compound of claim 1, which is:
HOOC—CH₂—NH-D-Cha-L-Pic-NH(CH₂)₂O—NH—C(=NH)NH₂ di(trifluoroacetate);
HO₂CCH₂—NH-L-Cha-L-Pic-NH(CH₂)₂O—NH—C(=NH)NH₂;
9-Hydroxy-9-fluorenylcarbonyl-L-Pro-NH(CH₂)₂O—NH—C(=NH)NH₂ trifluoroacetate; or
9-Hydroxy-9-fluorenylcarbonyl-L-Pro-NH(CH₂)₃O—NH—C(=NH)NH₂ trifluoroacetate;
or a solvate, hydrate, pharmaceutically acceptable salt or prodrug thereof.

34. A process for preparing an alkoxyguanidine compound of claim 1, comprising reacting an alkoxyamine derivatized dipeptide of the formula:

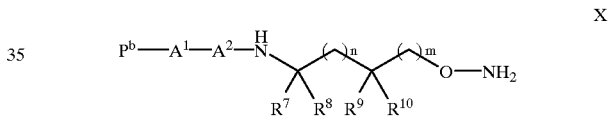

wherein $P^b$ is an amino protecting group, $A^1$, $A^2$, $R^7$–$R^{10}$, n and m are defined as in claim 1, with a guanidinylating reagent; and recovering said alkoxyguanidine compound.

35. The process of claim 34, wherein the guanidinylating reagent is selected from the group consisting of aminoiminosulfonic acid, optionally substituted 1H-pyrazole-1-carboxamidines, and N,N'-bis(tert-butoxycarbonyl)S-methyl isothiourea.

36. A pharmaceutical composition, comprising an amount of a compound of claim 1 or a pharmaceutical salt thereof, and a pharmaceutically acceptable carrier or diluent.

37. A method of inhibiting a serine protease, wherein said method comprises contacting a serine protease with a compound of claim 1.

38. A method of treating a mammal suffering from a loss of blood platelets; formation of blood platelet aggregates; formation of fibrin; thrombus formation; or embolus formation, wherein said method comprises administering to a mammal in need of said treating a composition of claim 36.

39. A method of treating a mammal suffering from myocardial infarction; unstable angina; stroke; restenosis; deep vein thrombosis; disseminated intravascular coagulation caused by trauma, sepsis or tumor metastasis; hemodialysis; hypercoagulability during chemotherapy; or fibrin formation in the eye, wherein said method comprises administering to a mammal in need of said treating a composition of claim 36.

* * * * *

UNITED STATES PATENT AND TRADEMARK OFFICE
CERTIFICATE OF CORRECTION

PATENT NO.    : 6,417,161 B1
DATED         : July 9, 2002
INVENTOR(S)   : Lu et al.

It is certified that error appears in the above-identified patent and that said Letters Patent is hereby corrected as shown below:

Column 20,
Line 60, in Figure *XII*, delete " 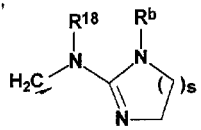 " and insert therefor -- 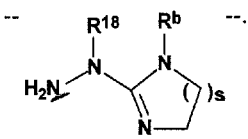 --.

*XII*                                                        *XII*

Column 33,
Lines 45-50, in Scheme 4, delete the chemical figure

" 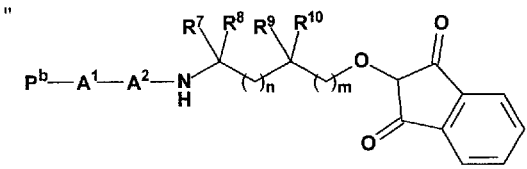 "

and insert therefor the chemical figure

-- 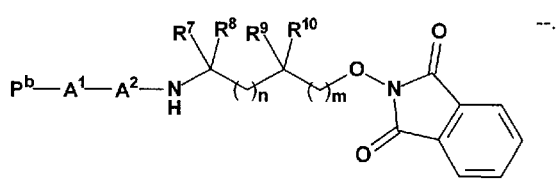 --.

Column 56,
Line 25, delete "$R^8$" and insert therefor -- $R^{48}$ --.

Column 57,
Line 56, delete "-$CH_2$-$CH_2$-" and insert therefor -- -$CH_2$-O-$CH_2$- --.
Line 58, delete "-$CH_2H_2$-$CH_2$-$CH_2$-" and insert therefor -- -$CH_2$-$CH_2$-$CH_2$-$CH_2$- --.
Line 59, delete "$R^3$ is as defined as for $R^4$ above;" and insert therefor -- $R^4$ is as defined as for $R^3$ above; --.

Column 58,
Line 35, delete "$R^c$" and insert therefor -- $R^e$ --.
Line 37, delete "$R^8$" and insert therefor -- $R^g$ --.

Column 60,
Line 57, delete "$R^{18}$" (second occurrence) and insert therefor -- $R^{10}$ --.
Line 65, delete "$R^{11}C$-$(C_{1-4})$alkyl-" and insert therefor -- $R^{11}OOC$-$(C_{1-4})$alkyl- --.

UNITED STATES PATENT AND TRADEMARK OFFICE
CERTIFICATE OF CORRECTION

PATENT NO. : 6,417,161 B1
DATED : July 9, 2002
INVENTOR(S) : Lu et al.

It is certified that error appears in the above-identified patent and that said Letters Patent is hereby corrected as shown below:

<u>Column 61,</u>
Line 50, delete "A compound of claim 23," and insert therefor -- A compound of claim 21, --.

<u>Column 63,</u>
Line 38, delete "HOOC-$CH_2CH_2$(HOOC-$CH_2$)R)Cha-Pro-" and insert therefor
-- HOOC-$CH_2$-$CH_2$(HOOC-$CH_2$)-(R)Cha-Pro --.

<u>Column 64,</u>
Line 2, delete "$(EtO)_2P(O)H_2$" and insert therefor

-- $(EtO)_2P(O)$-$CH_2$-(R)Cha-Pro-
    H-(R,S)Pro(3-(trans)Ch)-Pro-
    HOOC-$CH_2$-(R,S)Pro(3-(trans)Ph)-Pro-
    N-fluoren-9-ylcarboxy-Pro-
    N-(9-hydroxyfluoren-9-ylcarboxy)-Pro-
    Dca-Pro-
    Boc-Dca-Pro-
    Dpa-Pro-
    Boc-Dpa-Pro-
    $(Ph)_2CHCH_2C(O)$-Pro-
    $(Ph)_2CHC(O)$-Pro-
    $(Chx)_2CHCH_2C(O)$-Pro-
    $(Chx)_2CHC(O)$-Pro- . --.

Line 9, delete "n″ is 0 is and m´ is 0 or 1" and insert therefor -- n″ is 0 or 1 and m´ is 0 or 1. --.

Signed and Sealed this

Thirteenth Day of May, 2003

JAMES E. ROGAN
*Director of the United States Patent and Trademark Office*